United States Patent
Schneider et al.

(10) Patent No.: US 11,135,224 B2
(45) Date of Patent: Oct. 5, 2021

(54) METHODS OF SENSITIZING ESTROGEN RECEPTOR POSITIVE (ER+) BREAST CANCER CELLS TO ENDOCRINE THERAPY

(71) Applicant: New York University, New York, NY (US)

(72) Inventors: Robert J. Schneider, New York, NY (US); Phillip A. Geter, Belmont, CA (US); Sofia Bakogianni, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 109 days.

(21) Appl. No.: 16/723,573

(22) Filed: Dec. 20, 2019

(65) Prior Publication Data

US 2020/0197400 A1    Jun. 25, 2020

Related U.S. Application Data

(60) Provisional application No. 62/783,185, filed on Dec. 20, 2018.

(51) Int. Cl.

| | |
|---|---|
| *A61K 31/50* | (2006.01) |
| *A61K 31/47* | (2006.01) |
| *A61K 31/445* | (2006.01) |
| *A61P 35/00* | (2006.01) |
| *A61K 31/519* | (2006.01) |
| *C12N 5/09* | (2010.01) |
| *A61K 45/06* | (2006.01) |

(52) U.S. Cl.
CPC ............ *A61K 31/519* (2013.01); *A61K 45/06* (2013.01); *A61P 35/00* (2018.01); *C12N 5/0693* (2013.01); *C12N 2501/999* (2013.01)

(58) Field of Classification Search
CPC ...... A61K 31/50; A61K 31/47; A61K 31/445; A61P 35/00
USPC ..................... 514/252.06, 311, 321
See application file for complete search history.

(56) References Cited

U.S. PATENT DOCUMENTS

2011/0280886 A1    11/2011    Grzmil et al.

OTHER PUBLICATIONS

Geter et al., "Hyperactive mTOR and MNK1 Phosphorylation of eIF4E Confer Tamoxifen Resistance and Estrogen Independence Through Selective mRNA Translation Reprogramming," Genes Dev. 31:1-15 (Dec. 21, 2017).

*Primary Examiner* — Raymond J Henley, III
(74) *Attorney, Agent, or Firm* — Troutman Pepper Hamilton Sanders LLP (Rochester)

(57) ABSTRACT

Aspects of the technology are directed to a method of increasing sensitivity of estrogen receptor positive (ER⁺) breast cancer cells to treatment with an endocrine therapy. The method involves selecting ER⁺ breast cancer cells, and administering to the selected cells (i) one or more mammalian target of rapamycin (mTOR) inhibitors and (ii) one or more MAP kinase-interacting serine/threonine-protein kinase 1 (MNK1) inhibitors in an effective amount to increase the sensitivity of the ER⁺ breast cancer cells to treatment with the endocrine therapy. Methods of treating a subject having ER⁺ breast cancer are also disclosed.

20 Claims, 12 Drawing Sheets

METHODS OF SENSITIZING ESTROGEN RECEPTOR POSITIVE (ER+) BREAST CANCER CELLS TO ENDOCRINE THERAPY

This application claims the priority benefit of U.S. Provisional Patent Application Ser. No. 62/783,185, filed Dec. 20, 2018, which is hereby incorporated by reference in its entirety.

This invention was made with government support under R01CA207893 awarded by National Institutes of Health. The government has certain rights in the invention.

FIELD

Aspects of the technology described herein relate to methods of increasing sensitivity of estrogen receptor positive (ER$^+$) breast cancer cells to treatment with an endocrine therapy and to methods of treating a subject having ER$^+$ breast cancer.

BACKGROUND

Estrogen receptor-positive (ER$^+$) breast cancers comprise the majority (70%-80%) of breast cancers and the majority of breast cancer deaths resulting from metastatic disease (Fisher et al., "Treatment of Lymph-Node-Negative, Oestrogen-Receptor-Positive Breast Cancer: Long-Term Findings from National Surgical Adjuvant Breast and Bowel Project Randomized Clinical Trials," *Lancet* 364:858-868 (2004) and Early Breast Cancer Trialists' Collaborative Group, "Effects of Chemotherapy and Hormonal Therapy for Early Breast Cancer on Recurrence and 15-Year Survival: An Overview of the Randomised Trials," *Lancet* 365:1687-1717 (2005)). Anti-estrogen therapy with tamoxifen remains a cornerstone of therapy for ER$^+$ premenopausal breast cancer, but resistance occurs in a third of patients and often progresses to metastasis and death (Musgrove et al., "Biological Determinants of Endocrine Resistance in Breast Cancer," *Nat. Rev.* 9:631-643 (2009) and Droog et al., "Tamoxifen Resistance: from Bench to Bedside," *Eur. J. Pharmacol.* 717:47-57 (2013)). Estrogen receptor (ER) drives survival and proliferation pathways in breast cancer (Fullwood et al., "An Oestrogen-Receptor-α-Bound Human Chromatin Interactome," *Nature* 462:58-64 (2009)), functions as a nuclear hormone receptor responsible for integrating signals relayed by estrogen, and plays a critical role in breast cell transformation and carcinogenesis (Sommer et al., "Estrogen Receptor and Breast Cancer," *Semin. Cancer Biol.* 11:339-352 (2001)). Of the two main isoforms, ERα is implicated primarily in the onset of breast cancer (Sommer et al., "Estrogen Receptor and Breast Cancer," *Semin. Cancer Biol.* 11:339-352 (2001)). ERα binds transcriptional coactivators and regulators (e.g., NCOA1, NCOA2, and NCOA3) that specify differential transcriptional activity (Sommer et al., "Estrogen Receptor and Breast Cancer," *Semin. Cancer Biol.* 11:339-352 (2001); Oxelmark et al., "The Cochaperone p23 Differentially Regulates Estrogen Receptor Target Genes and Promotes Tumor Cell Adhesion and Invasion," *Mol. Cell. Biol.* 26:5205-5213 (2006); and Simpson et al., "High Levels of Hsp90 Cochaperone p23 Promote Tumor Progression and Poor Prognosis in Breast Cancer by Increasing Lymph Node Metastases and Drug Resistance," *Cancer Res.* 70:8446-8456 (2010)). Tamoxifen is an ER-antagonizing small molecule that blocks ER transcriptional activity (Osborne et al., "Selective Estrogen Receptor Modulators: Structure, Function, and Clinical Use," *J. Clin. Onco.* 18:3172-3186 (2000)) and inhibits ER$^+$ breast cancer cell proliferation and survival (Osborne et al., "Selective Estrogen Receptor Modulators: Structure, Function, and Clinical Use," *J. Clin. Onco.* 18:3172-3186 (2000)).

Most tamoxifen resistance in breast cancer does not involve loss of ERα receptor expression, although mutations are common (Garcia-Quiroz et al., "Calcitriol Reduces Thrombospondin-1 and Increases Vascular Endothelial Growth Factor in Breast Cancer Cells: Implications for Tumor Angiogenesis," *J. Steroid. Biochem. Mol. Biol.* 144: 215-222 (2014)). Tamoxifen resistance often involves hyperactivation of epidermal growth factor receptors (EGFRs) through a variety of mechanisms, including PI3K mutation and activation and MAPK-ERK activation (Campbell et al., "Phosphatidylinositol 3-Kinase/AKT-Mediated Activation of Estrogen Receptor α: a New Model for Anti-Estrogen Resistance," *J. Biol. Chem.* 276:9817-9824 (2001); Clark et al., "Constitutive and Inducible Akt Activity Promotes Resistance to Chemotherapy, Trastuzumab, or Tamoxifen in Breast Cancer Cells," *Mol. Cancer Ther.* 1:707-717 (2002); and Miller et al., "Hyperactivation of Phosphatidylinositol-3 Kinase Promotes Escape from Hormone Dependence in Estrogen Receptor-Positive Human Breast Cancer," *J. Clin. Invest.* 120:2406-2413 (2010)), resulting in uncoupled signaling from tamoxifen blockade (deGraffenried et al., "Inhibition of mTOR Activity Restores Tamoxifen Response in Breast Cancer Cells with Aberrant Akt Activity," *Clin. Cancer Res.* 10:8059-8067 (2004); Miller et al., "Phosphatidylinositol 3-Kinase and Antiestrogen Resistance in Breast Cancer," *J. Clin. Oncol.* 29:4452-4461 (2011); and Osborne et al., "Mechanisms of Endocrine Resistance in Breast Cancer," *Annu. Rev. Med.* 62:233-247 (2011)). Both EGFR and ERα signaling can hyperactivate the MAPK-ERK and mTOR pathways, which are known effectors of tamoxifen resistance (Schiff et al., "Cross-Talk Between Estrogen Receptor and Growth Factor Pathways as a Molecular Target for Overcoming Endocrine Resistance," *Clin. Cancer Res.* 10:331S-336S (2004); Massarweh et al., "Tamoxifen Resistance in Breast Tumors is Driven by Growth Factor Receptor Signaling with Repression of Classic Estrogen Receptor Genomic Function," *Cancer Res.* 68:826-833 (2008); Miller et al., "Hyperactivation of Phosphatidylinositol-3 Kinase Promotes Escape from Hormone Dependence in Estrogen Receptor-Positive Human Breast Cancer," *J. Clin. Invest.* 120:2406-2413 (2010); Miller et al., "Phosphatidylinositol 3-Kinase and Antiestrogen Resistance in Breast Cancer," *J. Clin. Oncol.* 29:4452-4461 (2011); Sabnis et al., "Adaptive Changes Results in Activation of Alternate Signaling Pathways and Resistance to Aromatase Inhibitor Resistance," *Mol. Cell. Endocrinol.* 340:142-147 (2011); Baselga et al., "Everolimus in Postmenopausal Hormone-Receptor-Positive Advanced Breast Cancer," *N. Engl. J. Med.* 366:520-529 (2012); Bostner et al., "Activation of Akt, mTOR, and the Estrogen Receptor as a Signature to Predict Tamoxifen Treatment Benefit," *Breast Cancer Res. Treat.* 137:397-406 (2013); Beelen et al., "Phosphorylated p-70S6K Predicts Tamoxifen Resistance in Postmenopausal Breast Cancer Patients Randomized Between Adjuvant Tamoxifen Versus no Systemic Treatment," *Breast Cancer Res.* 16:R6 (2014); Beelen et al., "PIK3CA Mutations, Phosphatase and Tensin Homolog, Human Epidermal Growth Factor Receptor 2, and Insulin-Like Growth Factor 1 Receptor and Adjuvant Tamoxifen Resistance in Postmenopausal Breast Cancer Patients," *Breast Cancer Res.* 16: R13 (2014); and Karthik et al., "mTOR Inhibitors Counteract Tamoxifen-Induced Activation of Breast Cancer Stem Cells," *Cancer Lett.* 367:76-87 (2015)). mTOR consist of two complexes: mTORC1 and mTORC2. mTORC1 regulates protein synthesis, lipid synthesis, and ribosome biogenesis (Dancey, "mTOR Signaling and Drug Development in Cancer," *Nat. Rev. Clin. Oncol.* 7:209-219 (2010) and Laplante et al., "mTOR Signaling in Growth Control and Disease," Cell 149:274-293 (2012)) and includes the proteins mTOR, Raptor, and GβL, among others (Sabatini, "mTOR and Cancer: Insights into a Complex Relationship," *Nat. Rev. Cancer* 6:729-734 (2006)). mTORC1 phosphorylates (inactivates) the negative regulator of cap-dependent mRNA translation known as the eIF4E-binding protein (4E-BP1). mTORC2 includes the proteins mTOR, Rictor, and GβL, among others; regulates cytoskeleton organization in response to growth signals; and promotes cell survival and proliferation through activation of AKT (Zoncu et al, "mTOR: From Growth Signal Integration to Cancer, Diabetes and Ageing," *Nat. Rev. Mol. Cell Biol.* 12:21-35 (2011)). Increased signaling through these pathways is often caused by up-regulated expression of EGFR and IGF-IR proteins, which is also seen in the majority of tamoxifen-resistant ER+ breast cancers and tamoxifen-resistant cell lines (Treeck et al., "Effects of a Combined Treatment with mTOR Inhibitor RAD001 and Tamoxifen in vitro on Growth and Apoptosis of Human Cancer Cells," *Gynecol. Oncol.* 102:292-299 (2006) and Cottu et al., "Acquired Resistance to Endocrine Treatments is Associated with Tumor-Specific Molecular Changes in Patient-Derived Luminal Breast Cancer Xenografts," *Clin. Cancer Res.* 20:4314-4325 (2014)).

Investigation of mTOR-directed endocrine resistance mechanisms have focused primarily on pathway cross-talk and activating upstream mutations. Phosphorylation by S6 kinase 1 (S6K1), a target of mTORC1, establishes endocrine-independent activation of ERα (Yamnik et al., "mTOR/S6K1 and MAPK/RSK Signaling Pathways Coordinately Regulate Estrogen Receptor α Serine 167 Phosphorylation," *FEBS Lett.* 584:124-128 (2010)). Similarly, EGFR activation by dimerization through activating mutations or ligands stimulates both mTORC1/2 and MAPK-ERK pathways and is also associated with tamoxifen and endocrine therapy resistance (Nicholson et al., "Growth Factor-Driven Mechanisms Associated with Resistance to Estrogen Deprivation in Breast Cancer: New Opportunities for Therapy," *Endocr. Relat. Cancer* 11:623-641 (2004). Moreover, increased AKT signaling is associated with resistance to anti-hormonal therapy, and, accordingly, inhibition of mTOR partially restores sensitivity (deGraffenried et al., "Inhibition of mTOR Activity Restores Tamoxifen Response in Breast Cancer Cells with Aberrant Akt Activity," *Clin. Cancer Res.* 10:8059-8067 (2004) and Beeram et al., "Akt-Induced Endocrine Therapy Resistance is Reversed by Inhibition of mTOR Signaling," *Ann. Oncol.* 18:1323-1328 (2007)). Furthermore, inhibiting both mTORC1/2 complexes blocks upstream AKT activation and increases resensitization to anti-endocrine agents (Leung et al., "MCF-7 Breast Cancer Cells Selected for Tamoxifen Resistance Acquire New Phenotypes Differing in DNA Content, phospho-HER2 and PAX2 Expression, and Rapamycin Sensitivity," *Cancer Biol. Ther.* 9:717-724 (2010) and Jordan et al., "Impact of Dual mTORC1/2 mTOR Kinase Inhibitor AZD8055 on Acquired Endocrine Resistance in Breast Cancer in vitro," *Breast Cancer Res.* 16:R12 (2014)). However, little is known regarding the molecular basis for tamoxifen resistance downstream from mTOR, apart from pathway cross-talk. Downstream effectors of mTOR activity in tamoxifen and endocrine resistance remain unknown. mTOR and ERK signaling pathways converge on the control of mRNA translation (Silvera et al., "Translational Control in Cancer," *Nat. Rev. Cancer* 10:254-266 (2010)). Translation of mRNA begins with recognition of the 5' inverted methyl$^7$-GTP "cap" structure by the translation initiation complex consisting of cap-binding protein eIF4E, RNA helicase eIF4A, and scaffolding protein eIF4G, which recruits the 40S ribosomal subunit and other initiation factors. Many of the translation initiation factors are regulated by mTORC1 activity. In particular, mTOR hyperphosphorylates the 4E-BPs (4E-BP1 is the major form in epithelial cells), preventing them from sequestering eIF4E by competing with the scaffolding protein eIF4G, thereby promoting translation. mRNA translation is also regulated by the MAPK/ERK pathway in response to growth factors, cytokines, and oncogenic signaling (Topisirovic et al., "Translational Control by the Eukaryotic Ribosome," *Cell* 145:333-334 (2011)). ERK acts on mRNA translation by activating the eIF4G-associated kinase MNK1. MNK1 phosphorylates eIF4E at S209, which is associated with increased transformation potential, although a mechanism is lacking (Wendel et al., "Dissecting eIF4E Action in Tumorigenesis," *Genes Dev.* 21:3232-3237 (2007); Silvera et al., "Translational Control in Cancer," *Nat. Rev. Cancer* 10:254-266 (2010); Wheater et al., "The Role of MNK Proteins and eIF4E Phosphorylation in Breast Cancer Cell Proliferation and Survival," *Cancer Biol. Ther.* 10:728-735 (2010); Konicek et al., "Therapeutic Inhibition of MAP Kinase Interacting Kinase Blocks Eukaryotic Initiation Factor 4E Phosphorylation and Suppresses Outgrowth of Experimental Lung Metastases," *Cancer Res.* 71:1849-1857 (2011); Topisirovic et al., "Translational Control by the Eukaryotic Ribosome," *Cell* 145:333-334 (2011); and Wolfe et al., "RNA G-Quadruplexes Cause eIF4A-Dependent Oncogene Translation in Cancer," *Nature* 513:65-70 (2014)). The nature of the increased requirement for eIF4E with malignancy is thought to involve selective mRNA translation, but the mechanism is complex and remains only partially understood (Waskiewicz et al., "Phosphorylation of the Cap-Binding Protein Eukaryotic Translation Initiation Factor 4E by Protein Kinase Mnk1 in vivo," *Mol. Cell. Biol.* 19:1871-1880 (1999); Topisirovic et al., "mRNA Translation and Energy Metabolism in Cancer: The Role of the MAPK and mTORC1 Pathways," *Cold Spring Harb. Symp. Quant. Biol.* 76:355-367 (2011); and Bhat et al., "Targeting the Translation Machinery in Cancer," *Nat. Rev. Drug. Discov.* 14:261-278 (2015)). Up-regulation of the abundance and/or activity of eIF4E, eIF4A, and/or eIF4G occurs widely in breast and other cancers and selectively up-regulates translation of certain mRNAs involved in survival, proliferation, and metastasis (Avdulov et al., "Activation of Translation Complex eIF4F is Essential for the Genesis and Maintenance of the Malignant Phenotype in Human Mammary Epithelial Cells," *Cancer Cell* 5:553-563 (2004); Braunstein et al., "A Hypoxia-Controlled Cap-Dependent to Cap-Independent Translation Switch in Breast Cancer," *Mol. Cell* 28:501-512 (2007); Kim et al., "Eukaryotic Initiation Factor 4E Binding Protein Family of Proteins: Sentinels at a Translational Control Checkpoint in Lung Tumor Defense," *Cancer Res.* 69:8455-8462 (2009); Silvera et al., "Translational Control in Cancer," *Nat. Rev. Cancer* 10:254-266 (2010); Badura et al., "DNA Damage and eIF4G1 in Breast Cancer Cells Reprogram Translation for Survival and DNA Repair mRNAs," *Proc. Natl. Acad. Sci.* 109:18767-18772 (2012); and Decarlo et al., "eIF4E is a Feed-Forward Translational Coactivator of TGFβ Early Pro-Transforming Events in Breast Epithelial Cells," *Mol. Cell. Biol.* 35:2597-2609 (2015)). In fact, increased abundance of eIF4E has been shown to be important in resistance to a variety of PI3K-

AKT-mTOR inhibitors (Avdulov et al., "Activation of Translation Complex eIF4F is Essential for the Genesis and Maintenance of the Malignant Phenotype in Human Mammary Epithelial Cells," *Cancer Cell* 5:553-563 (2004); Kim et al., "Eukaryotic Initiation Factor 4E Binding Protein Family of Proteins: Sentinels at a Translational Control Checkpoint in Lung Tumor Defense," *Cancer Res.* 69:8455-8462 (2009); Silvera et al., "Inflammatory Breast Cancer Pathogenesis Mediated by Translation Initiation Factor eIF4G Overexpression and Unorthodox Protein Synthesis," *Nat. Cell Biol.* 11:903-910 (2009); Silvera et al., "Translational Control in Cancer," *Nat. Rev. Cancer* 10:254-266 (2010); Bitterman et al., "Translational Control of Cancer: Implications for Targeted Therapy," Polunovsky, *mTOR Pathway and mTOR Inhibitors in Cancer Therapy*, pp. 237-255. New York: Springer (2010); Hsieh et al., "The Translational Landscape of mTOR Signalling Steers Cancer Initiation and Metastasis," *Nature* 485:55-61 (2012); Ilic et al., "PI3K-Targeted Therapy can be Evaded by Gene Amplification Along the MYC-Eukaryotic Translation Initiation Factor 4E (eIF4E) Axis," *Proc. Natl. Acad. Sci.* 108:E699-E708 (2010); Burris, "Overcoming Acquired Resistance to Anticancer Therapy: Focus on the PI3K/Akt/mTOR Pathway," *Cancer Chemother. Pharmacol.* 71: 829-842 (2013); Bhat et al., "Targeting the Translation Machinery in Cancer," *Nat. Rev. Drug. Discov.* 14:261-278 (2015); and Fagan et al., "Acquired Tamoxifen Resistance in MCF-7 Breast Cancer Cells Requires Hyperactivation of eIF4F-Mediated Translation," *Horm. Cancer* 8:219-229 (2017)).

Certain mRNAs possess long or structured 5' untranslated regions (UTRs) that serve to more highly regulate their translation and often encode transforming and survival proteins important for cancer development and progression (Koromilas et al., "mRNAs Containing Extensive Secondary Structure in Their 5' Non-Coding Region Translate Efficiently in Cells Overexpressing Initiation Factor eIF-4E," *EMBO 1* 11:4153-4158 (1992); Svitkin et al., "Eukaryotic Translation Initiation Factor 4E Availability Controls the Switch Between Cap-Dependent and Internal Ribosomal Entry Site-Mediated Translation," *Mol. Cell. Biol.* 25:10556-10565 (2005); and Badura et al., "DNA Damage and eIF4G1 in Breast Cancer Cells Reprogram Translation for Survival and DNA Repair mRNAs," *Proc. Natl. Acad. Sci.* 109:18767-18772 (2012)). These mRNAs typically display a greater requirement for eIF4E, often a result of increased secondary structure close to the cap (Koromilas et al., "mRNAs Containing Extensive Secondary Structure in Their 5' Non-Coding Region Translate Efficiently in Cells Overexpressing Initiation Factor eIF-4E," *EMBO J.* 11:4153-4158 (1992); Badura et al., "DNA Damage and eIF4G1 in Breast Cancer Cells Reprogram Translation for Survival and DNA Repair mRNAs," *Proc. Natl. Acad. Sci.* 109:18767-18772 (2012); and Hsieh et al., "The Translational Landscape of mTOR Signalling Steers Cancer Initiation and Metastasis," *Nature* 485:55-61 (2012)). Certain sequence motifs are also thought to increase the requirement for eIF4E interaction, although direct binding by eIF4E has not been shown (Hsieh et al., "The Translational Landscape of mTOR Signalling Steers Cancer Initiation and Metastasis," *Nature* 485:55-61 (2012)).

There remains a great need to elucidate the mechanism of ER$^+$ cancer progression and development. There also remains a need for more effective targeted therapies that can overcome challenges associated with the current endocrine therapies, while optionally providing further benefits by combining with additional therapeutic agents to combat cancer.

The present invention is directed to overcoming these and other deficiencies in the art.

SUMMARY

One aspect of the technology described herein relates to a method of increasing sensitivity of estrogen receptor positive (ER$^+$) breast cancer cells to treatment with an endocrine therapy. The method involves selecting ER$^+$ breast cancer cells, and administering to the selected cells (i) one or more mammalian target of rapamycin (mTOR) inhibitors and (ii) one or more MAP kinase-interacting serine/threonine-protein kinase 1 (MNK1) inhibitors. The administering of (i) and (ii) to the selected cells is in an effective amount to increase the sensitivity of the ER$^+$ breast cancer cells to treatment with the endocrine therapy.

Another aspect of the technology described herein relates to a method of treating a subject having ER$^+$ breast cancer. The method involves selecting a subject having ER$^+$ breast cancer, where the ER$^+$ breast cancer exhibits resistance to treatment with an endocrine therapy, and administering to the selected subject (i) one or more mTOR inhibitors, (ii) one or more MNK1 inhibitors, and (iii) one or more endocrine therapies, thereby treating the subject.

The majority of breast cancers expressing the estrogen receptor (ER$^+$) are treated with anti-estrogen therapies, particularly tamoxifen in premenopausal women. However, tamoxifen resistance is responsible for a large proportion of breast cancer deaths. Using small molecule inhibitors, phospho-mimetic proteins, tamoxifen-sensitive and tamoxifen-resistant breast cancer cells, a tamoxifen-resistant patient-derived xenograft model, patient tumor tissues, and genome-wide transcription and translation studies, the Examples of the present application (infra) demonstrate that tamoxifen resistance involves selective mRNA translational reprogramming to an anti-estrogen state by Runx2 and other mRNAs. Tamoxifen-resistant translational reprogramming is shown to be mediated by increased expression of eIF4E and its increased availability by hyperactive mTOR and to require phosphorylation of eIF4E at Ser209 by increased MNK activity. Resensitization to tamoxifen is shown to be restored by reducing eIF4E expression or mTOR activity and also blocking MNK1 phosphorylation of eIF4E. mRNAs specifically translationally up-regulated with tamoxifen resistance include Runx2, which inhibits ER signaling and estrogen responses and promotes breast cancer metastasis. Silencing Runx2 significantly restores tamoxifen sensitivity. Tamoxifen-resistant but not tamoxifen-sensitive patient ER$^+$ breast cancer specimens also demonstrate strongly increased MNK phosphorylation of eIF4E. Data herein demonstrates that eIF4E levels, availability, and phosphorylation promote tamoxifen resistance in ER$^+$ breast cancer through selective mRNA translational reprogramming.

As demonstrated by the accompanying Examples, tamoxifen resistance involves genome-wide translational reprogramming to select for the translation of mRNAs that specifically provide anti-estrogen and ER activities and requires increased expression and availability of eIF4E and its increased phosphorylation by MNK1. Blockade of both mTORC1 and MNK1 re-establishes tamoxifen sensitivity and blocks selective translation of the small group of mRNAs that provide tamoxifen resistance. The present invention provides a significant step forward in the treatment of ER$^+$ breast cancer.

BRIEF DESCRIPTION OF THE DRAWINGS

FIG. 1A shows cell cycle analysis performed on the TamS and TamR cells treated with either DMSO control or 1 μM 4-OH Tam for 72 hours in 1% CS-FBS. Cells were fixed in 70% ethanol overnight. Cells were subjected to RNaseA treatment and stained with propidium iodide (PI). Data was collected using FACScalibur and analyzed with FloJo 10.0 software. Data from 3 independent experiments are shown. SEMs are shown. P<0.01 and *P<0.001 by two-way ANOVA. FIG. 1B shows cell proliferation as assayed by MTT assay initiated 24 hours after plating (day 0). TamS and TamR cells were treated with either DMSO or 1 μM 4-OH Tam and initiated on day 0. Results are representative of 3 independent experiments and presented as relative proliferation in which all samples are normalized to Day 0. Standard deviations are shown. *P<0.05 by t-test. FIG. 1C shows the results of a colony survival assay performed by low density seeding (1000 cells) of TamS and TamR cells. Cells were treated with either DMSO or 1 μM 4-HT 24 hours after plating. Colonies scored after 10 days counting only ≥50 cells/colony. Results are representative of 3 independent experiments. SEMs are shown. ***P<0.001 by two-way ANOVA. FIG. 1D shows cell cycle analysis performed as described in FIG. 1A on BR7 (PDX) cells treated with either DMSO control or 1 μM 4-OH Tam (n.s.=not significant). FIG. 1E shows the expression of c-Myc and EEIG1 mRNA in MCF7/TamS and MCF7/TamR cells following treatment with either DMSO or Tam for 24 hours. Equal amounts of RNA were reverse transcribed and quantified through real-time PCR. RNA levels normalized to GAPDH using the $^{-\Delta\Delta}Ct$ method. Error bars represent SEM. FIG. 1F shows results for an experiment performed as in FIG. 1E on BR7 (PDX) cells following treatment with either DMSO or Tam for 24 hours. RNA levels normalized to GAPDH using the $^{-\Delta\Delta}Ct$ method. Error bars represent SEM.

FIG. 2A shows an immunoblot of TamS and TamR cells lysed in NP-40 buffer during exponential growth and probed for mTORC1 target proteins. β-Actin was used as a loading control. FIG. 2B shows an immunoblot of representative TamS and TamR cells lysed in NP-40 buffer and probed for the eIF4F complex proteins. eIF4Awas also used as a loading control. FIG. 2C shows immunoblot analysis of protein lysates from TamS and TamR cells following 4-hydroxytamoxifen (4-OHT) treatment in serum-free medium. Cells were treated using serum-free medium, with the 0 time point indicating untreated control samples using ImageJ software. eEF2 was used as a loading control. The bracketed eIF4E-P and eIF4E blots were normalized to loading equal levels of eIF4E. All other blots used equal protein amounts. The image is representative of three independent experiments. FIG. 2D shows results from an experiment in which NP40 cytoplasmic protein extracts were subjected to immunoblot. Representative results comparing TamS with BR7 PDX cells are shown. eIF4E-P and eIF4E blots were normalized to loading equal levels of eIF4E. All other blots used equal protein amounts. FIG. 2E is a table showing the overall protein synthesis activity of TamS and TamR cells as measured by [$^{35}$S]-methionine metabolic labeling normalized to TamR cells. A representative of three independent experiments is shown in FIG. 2E (n.s.=not significant). FIG. 2F shows immunohistochemical staining of representative recurrent and nonrecurrent tumor specimens for P-4E-BP1 (S65), P-S6 (S235/236), PeIF4E (S209), and total eIF4E. Bar, 20 μm. The immunoblots shown are representative of three independent experiments.

FIG. 3A shows an immunoblot of equal amounts of protein from TamS and TamR cells during exponential growth. Cells were lysed in NP-40 buffer and probed for key translation factors. β-tubulin (loading control). FIG. 3B shows results of a colony survival assay performed by low density seeding (1000 cells) of stably transduced TamR cells (sh-control or sh-eIF4E-2). Cells were treated with either DMSO or 1 μM 4-OH Tam 24 hours after plating. Dox (1 μg/mL) was administered 24 hours after plating and removed after 72 hours. Colonies scored after 10 days counting only ≥50 cells/colony. SEM is shown. FIG. 3C shows results of cell cycle analysis performed on TamR cells following eIF4E silencing (sh-eIF4E-2). Cells were treated with either DMSO control or 1 μM 4-OH Tam for 72 hours in 1% CS-FBS. Dox (1 μg/mL) was administered to cells for 72 hours. Cells were fixed in 70% ethanol overnight and subjected to RNaseA treatment. Cells were stained with Hoechst 33342. Data was collected using LSRII UV and analyzed with FloJo software. Data from 3 independent experiments are shown. SEM is shown. *P<0.05 by two-way ANOVA. FIG. 3D shows data demonstrating that overexpressing 4E-BP1 in breast cancer cells increases its association with eIF4E. Cap chromatography performed on TamR cells with or without 4E-BP1 cDNA overexpression. Cells were lysed in NP-40 buffer and pulldown was performed for 1 hour at 4° C. Proteins were eluted and resolved via SDS-PAGE. Membrane was probed for eIF4E, eIF4GI and 4E-BP1. A representative blot is shown in FIG. 3D. FIG. 3E shows results of cell cycle analysis performed on the BR7 (PDX) cells treated with either DMSO control or 1 μM 4-OH Tam for 72 hours in 1% CS-FBS with or without eIF4E silencing. Cells were fixed in 70% ethanol overnight. Cells were subjected to RNaseA treatment and stained with propidium iodide (PI). Data was collected using FACScalibur and analyzed with FloJo 10.0 software. BR7 cells were transfected with 25 nM of either non-targeting (NT) or eIF4E specific siRNA for 72 hours. Cells were lysed in NP-40 buffer and equal amounts of protein were resolved via SDS-PAGE and transferred to a PVDF membrane. Membrane was probed for eIF4E. β-actin (loading control). FIG. 3F shows results of cell cycle analysis performed on TamR cells treated with DMSO control, 1 μM 4-OH Tam, or 4-OH Tam and RAD001 (20 nM) for 72 hours in 1% CS-FBS. Cells were fixed in 70% ethanol overnight. Cells were subjected to RNaseA treatment and stained with propidium iodide (PI). Data was collected using FACScalibur and analyzed with FloJo 10.0 software. Data from three independent experiments are shown in FIG. 3F. SEM is shown. *P<0.05 by two-way ANOVA. FIG. 3G shows the results of a colony survival assay performed by low density seeding (1000 cells) of TamS and TamR cells. Cells were treated with DMSO, 1 μM 4-OH Tam, 20 nM RAD001, or combination therapy 24 hours after plating. Treatment was changed every 72 hours. Colonies scored after 10 days counting only ≥50 cells/colony. Results shown in FIG. 3G are representative of three independent experiments. SEM is shown.

FIG. 4A shows mRNA expression of eIF4E in TamR cells following 72 hours of 1 μg/mL Dox induction of eIF4E shRNAs. Equal amounts of RNA were quantified by quantitative real-time PCR (RT-qPCR) and normalized to GAPDH using the $-\Delta\Delta Ct$ method.

FIG. 4B is an immunoblot of equal amounts of protein from NP-40-extracted TamS and TamR sh-control or sh-eIF4E cells 72 hours after Dox addition. β-Actin was used as a loading control. Representative immunoblots are shown. FIG. 4C shows the overall protein synthesis activity of TamS and TamR cells with or without eIF4E silencing by [$^{35}$S]-methionine metabolic labeling. Three independent studies were averaged. (*)P<0.05 by two-way ANOVA (n.s.=not significant). FIG. 4D shows results of a colony survival growth assay that was performed by low-density seeding (1000 cells) of stably transduced TamS and TamR cells treated with vehicle (DMSO) or 1 µM 4-OHT 24 hours after plating. Dox (1 µg/mL) was administered 24 hours after plating and removed at 72 hours. Colonies were scored after 10 days, counting only ≥50 cells per colony. Results from three independent experiments were normalized to DMSO control. ()P<0.01. Comparisons were by two-way ANOVA. FIG. 4E shows representative immunoblot of equal amounts of protein lysate from 4E-BP1-overexpressing cells. Dox (1 µg/mL) was added 72 hours prior to lysis in NP-40 buffer. β-Actin was used as a loading control. FIG. 4F shows results of colony survival assays that were performed as in FIG. 4D after plating with Dox-induced 4E-BP1 expression. ()P<0.01; (*)P<0.001 by two-way ANOVA. FIG. 4G shows results of an experiment in which cell proliferation was assayed with Dox-induced overexpression of 4E-BP1. Cell proliferation was assayed by MTT and treated with vehicle (DMSO) or 1 µM4-OHT. Dox was added at day 0 to induce 4E-BP1 expression. Results from three independent experiments were normalized to day 0. ()P<0.01; (***)P<0.001 by t-test.

FIG. 5A shows an immunoblot analysis of equal amounts of protein from TamS and TamR cells transfected with eIF4E phospho-mutants S209A or S209D, respectively or a control vector. Hsp70 (loading control). FIG. 5B shows the results of an experiment in which TamR cells were untreated or treated with 10 µM CGP57380 for 6 hours and equal protein amounts immunoblotted as shown. FIG. 5C shows the results of a colony survival assay performed by low density seeding (1000 cells) of TamS and TamR cells. Cells were treated with DMSO, 1 µM 4-OH Tam, 4-OH Tam and CGP 57380 (10 µM), or 1 µM 4-OH Tam, CGP57380, and 20 nM RAD001 therapies 24 hours after plating. Treatment was changed every 72 hours. Colonies were scored after 10 days counting only >50 cells/colony. Results are representative of three independent experiments. SEM is shown. FIG. 5D shows the overall protein synthesis activity of the TamS and TamR cells was measured by [$^{35}$S]-methionine labeling for 30 minutes, following treatment with either DMSO or 10 µM CGP 57380 for 24 hours. Results from three independent experiments. Error bars represent SEM (n.s.=not significant). FIG. 5E shows the results of polysomal profiling performed on TamR cells treated with either DMSO or 10 µM CGP57380 for 24 hours. Equal amounts of RNA were resolved by sucrose gradient centrifugation and ribosome profiles monitored by UV absorbance 254 nm. Results are representative images of two independent experiments.

FIG. 6A shows results from an experiment in which TamS cells were transfected with either empty vector or an eIF4E 5209D-expressing construct 48 hours prior to proliferation assay. Endogenous eIF4E was silenced by shRNA. Cell proliferation was assayed by MTT assay with cells treated with DMSO vehicle or 1 µM 4-OHT. Results are from three independent experiments. FIG. 6B shows results from an experiment in which TamR cells were transfected with empty vector or eIF4E 5209A-expressing vector 48 hours prior to proliferation assay. Endogenous eIF4E was silenced by shRNA. Cell proliferation was assayed by MTT assay using conditions described above for FIG. 4. Results from three independent experiments are shown. FIG. 6C is an immunoblot of TamS and TamR cells treated with escalating doses of CGP57380 (GCP) for 2 hours and lysed in NP-40 buffer; equal protein amounts were probed for P-eIF4E, total eIF4E, and β-actin (loading control). FIG. 6D shows the results of an experiment in which cell proliferation was assayed as above. Cells were treated with DMSO, 1 µM 4-OHT, or 4-OHT and MNK1 inhibitor CGP. Results of three independent experiments are shown. (**)P<0.01 by t-test. FIG. 6E shows results from colony survival assays performed as described above for FIG. 4. Cells were treated with DMSO, 1 µM 4-OHT, 10 µM CGP, or combination therapy 24 hours after plating. Drugs were restored every 72 hours. Data from three independent experiments were normalized to DMSO control. (*) P<0.05; ()P<0.01; (*) P<0.001 by two-way ANOVA; (n.s.=not significant). FIG. 6F shows the results from TamR colony survival assays performed as described above for FIG. 4 and treated as in FIG. 6E plus 20 mM RAD001. Data from three independent experiments were normalized to DMSO control. (**)P<0.01 by t-test.

FIG. 7A shows a representative immunoblot analysis of equal amounts of protein lysate from eIF4E-overexpressing cells. Dox (2 µg/mL) was added 72 hours prior to lysis in NP-40 buffer. Equal protein amounts were immunoblotted as shown. β-Actin was used as a loading control. FIG. 7B shows cell cycle analysis of TamS control and TamS cells overexpressing eIF4E and treated with DMSO (vehicle) or 1 µM 4-OHT for 72 h in 1% CS-FBS. Dox (2 µg/mL) was added for 72 hours. Cells were subjected to exhaustive RNase A and stained with propidium iodide (PI). Flow cytometry data were collected using a FACSCalibur and analyzed with FloJo software. The average of three studies is shown. FIG. 7C shows immunoblot analysis of mTORC1 pathway proteins in TamS control, eIF4E-overexpressing, TSC2 silenced, or TSC2 silenced and eIF4E-overexpressing cells. Cells were treated with 2 µg/mL Dox for 72 hours and lysed in NP-40 buffer. Equal protein amounts were immunoblotted. β-Actin was used as a loading control. Representative results are shown. FIG. 7D shows results of colony survival assays from three studies performed as described above for FIG. 4. TamS sh-control, eIF4E-overexpressing, shTSC2, and shTSC2 and eIF4E-overexpressing cells were treated with either DMSO or 1 µM 4-OHT. ()P<0.01; (*)P<0.0001 by two-way ANOVA. FIG. 7E shows the quantitation of eIF4E S209 phosphorylation in the cells treated in FIG. 7C. FIG. 7F shows the quantification of markers of ER signaling in TamS cells by RTqPCR of mRNAs with cDNA overexpression of eIF4E, shRNA silencing of TSC2, or both. Results are the average of three independent studies.

FIGS. 8A-8B show genome-wide transcription and translation mRNA profiling of TamS compared with TamR cells with 1 μM 4-OHT for 48 hours. Results are from two independent studies. Total mRNA and purified fractions containing four or more bound ribosomes (heavy) were sequenced using Illumina HiSeq 2500 single read. Volcano plots represent differences in transcription (FIG. 8A) and translation (FIG. 8B). Light grey dots identify mRNAs significantly changed in abundance. Transcription parameters were P≤0.05 and −1.0≤log$_2$≥1.0, translation parameters were P≤0.05 and −0.6≤log$_2$≥0.6. Dark grey dots identify mRNAs not significantly changed in abundance. Statistical analysis was performed using the limma R package. FIGS. 8C-8D show that the top molecular functions of mRNAs are significantly altered in total abundance and translation from heavy (well-translated) fractions (four or more ribosomes), respectively. FIGS. 8E-8F show that the top biological functions of mRNAs are significantly altered in total abundance and translation from heavy (well-translated) fractions (four or more ribosomes), respectively. FIG. 8G shows the relative pathway summation of transcriptional and translational changes in mRNAs in TamR cells relative to TamS cells.

FIG. 9A shows the polysome profiles of TamR cells without and with eIF4E silencing. Representative results are shown. FIG. 9 inset is an immunoblot showing eIF4E levels and control β-actin. FIGS. 9B-9C show genome-wide transcription and translation mRNA profiling of TamR cells with or without eF4E silencing plus 1 μM 4-OHT for 48 hours. Results are from two independent studies. Total mRNA and purified fractions containing four or more bound ribosomes (heavy) were sequenced and analyzed using the same parameters as described above for FIG. 8. FIGS. 9D-9E are charts showing the top molecular functions of mRNAs significantly altered in total abundance (FIG. 9D) and in translation (FIG. 9E) from heavy (well-translated) fractions (four or more ribosomes), respectively. FIG. 9F is a chart showing the top biological functions of mRNAs significantly altered in translation from heavy polyribosomes.

FIG. 10A is a heatmap (generated using GENE-E software) of genes altered in total abundance or translation (light and heavy polysome) with eIF4E silencing from TamR cells. Dark grey indicates an increase and light grey a decrease in expression. FIG. 10B shows results of RNA-seq validated using RT-qPCR analysis. The plot shows the correlation of gene expression between the RNA-seq and qPCR analysis (qPCR values are a mean of log$_2$ fold change+/−SD) from the total extracted mRNA. Pearson's correlation ($R^2$) is shown on each graph. Dotted lines represent significance cutoffs. FIG. 10C shows the results of RNA-seq validated using RT-qPCR analysis. The plot shows the correlation of gene expression between the RNA-seq and qPCR analysis (qPCR values are a mean of log$_2$ fold change+/−SD) of mRNAs extracted from heavy (≥4 ribosomes) polysome fractions. Pearson's correlation ($R^2$) is shown on each graph. Dotted lines represent significance cutoffs. FIG. 10D shows a graph representing the top downregulated biological pathways from the total mRNA fraction with eIF4E silencing in TamR cells. Numbers above bars represent P-values. FIG. 10E shows a graph representing the top downregulated biological pathways from the heavy polysome fraction with eIF4E silencing in TamR cells. Numbers above bars represent P-values. FIG. 10F is a graph representing the top upregulated biological pathways from the total mRNA fraction with eIF4E silencing in TamR cells. Numbers above bars represent P-values. FIG. 10G is a graph representing the top upregulated biological pathways from the heavy polysome fraction with eIF4E silencing in TamR cells. Numbers above bars represent P-values. Pathways were identified using Ingenuity Pathway Analysis (IPA) software (FIGS. 10D-10E). FIG. 10H shows the predicted structure of Runx2 5'UTR using mfold web server. Computational folding was done under standard thermodynamic conditions. Analysis was repeated using both RNA structure and IDT UNAFold folding programs. Similar structural and thermodynamic results were returned. The ΔG value represents that predicted by mfold.

FIG. 11A shows the relative levels of Runx2 mRNA and levels in heavy polysomes in TamR compared with TamS cells. FIG. 11B shows the levels of Runx2 mRNA and protein in BR7 compared with TamS cells. mRNA levels were determined by RT-qPCR, as above. The average of three studies is shown. The immunoblot is representative of three independent studies. FIG. 11C shows the relative levels of Runx2 mRNA in total and heavy polysomes in TamR cells in Dox-inducible sh-control non-silencing (NS) and sh-eIF4E silencing for 72 hours. Equal amounts of RNA were quantified by RT-qPCR and normalized to GAPDH using the −ΔΔCt method. An average of three studies is shown. FIG. 11D shows a representative immunoblot analysis of equal amounts of protein lysate from TamR cells silenced with nonsilencing (NS) control or sh-eIF4E for 72 hours. Equal protein amounts were immunoblotted as shown. eEF2 was used as a loading control. FIG. 11E shows results from experiments in which TamS and TamR cells were treated with CGP57380 for 6 hours, and equal protein amounts of lysates were examined by immunoblot as shown. FIG. 11F shows results from experiments in which relative levels of Runx2 mRNA in TamR cells silenced with nonsilencing (NS) control or sh-Runx2 were analyzed as above. FIG. 11G shows results from experiments in which cell proliferation was assayed as described above for FIG. 4. Cells were treated with DMSO and 1 μM4-OHT and silenced for Runx2 or nonsilencing (NS). The results of three independent experiments are shown. FIG. 11H shows a colony survival assays from three studies were performed as described above for FIG. 4 using TamR cells with sh-nonsilencing (sh-NS) control or sh-Runx2 in the presence of 1 μM 4-OHT. FIG. 11I shows STRING analysis of the top 20 protein interactors of the Runx2-ERα complex. Lines represent validated and predicted interactions. FIG. 11J shows levels of identified mRNAs in TamR cells treated with DMSO, 1 μM 4-OHT, or 4-OHT and silenced for Runx2 or nonsilencing (NS) after 72 hours of treatment. ()P<0.01; (*)P<0.001 by t-test.

FIG. 12A is a histogram that represents a genome-wide analysis of the GC percentage (normalized to 5'UTR length) of the 5' UTRs from all mRNAs or downregulated mRNAs extracted from the heavy polysome fraction. mRNAs were extracted from TamR sh-control and sh-eIF4E cells. FIG. 12B is a histogram that represents a genome wide analysis of the length of the 5' UTRs from all mRNAs or downregulated mRNAs extracted from the heavy polysome fraction. mRNAs were extracted from TamR sh-control and sh-eIF4E cells. Histograms generated using R studio software. FIG. 12C is a heatmap generated from TCGA analysis of Runx2 and ER (ESR1) mRNA expression from patients (n=594) diagnosed with ER⁺ breast cancer. FIG. 12D shows qRT-PCR analysis of Runx2 and ER (ESR1) mRNA in breast cancer cell lines (left panel). Zoomed comparison of Runx2 mRNA levels in TamS and TamR cells (right panel).

DETAILED DESCRIPTION

Figures 1A, 1B, 1C, 1D, 1E, 1F:
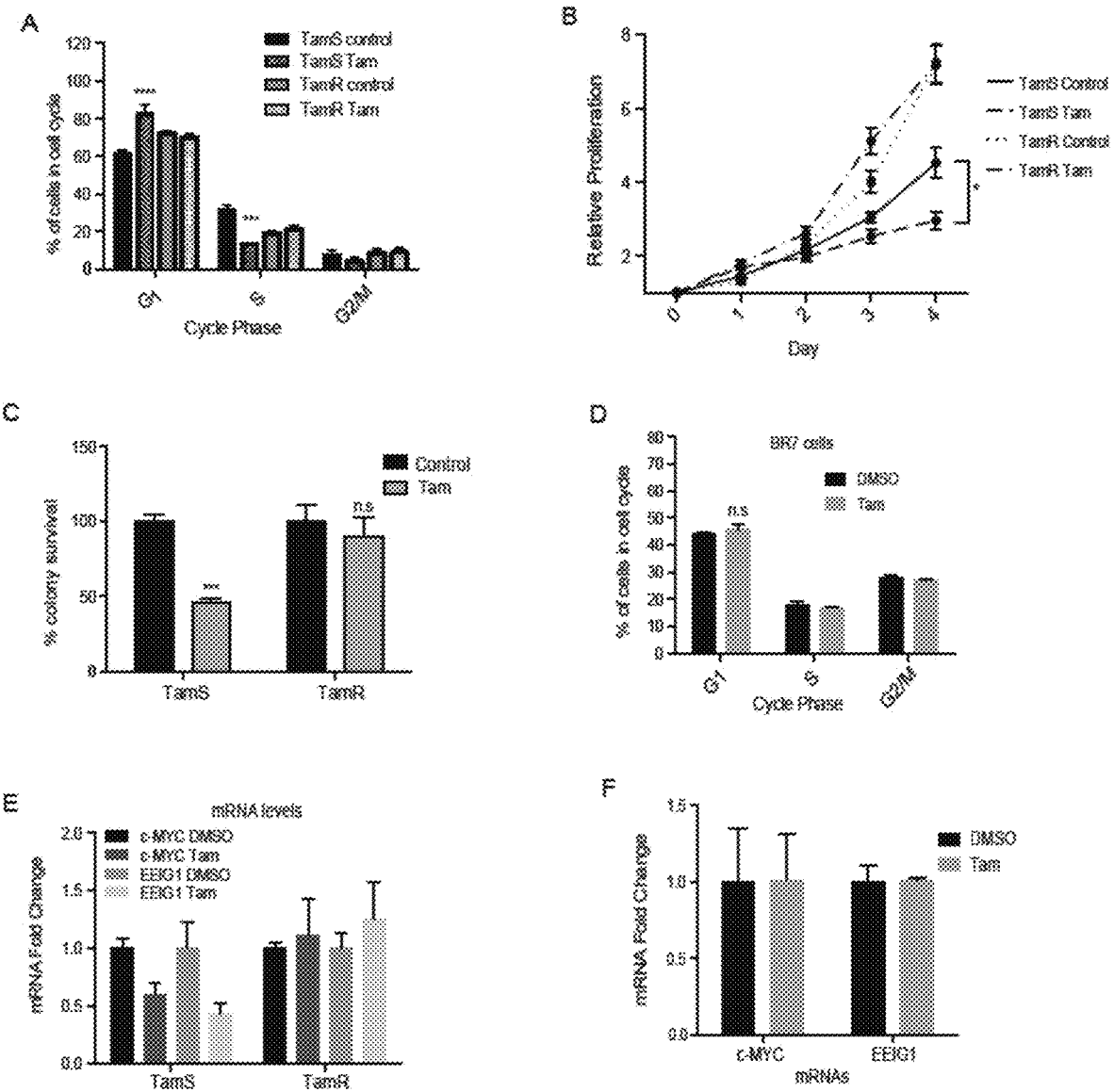
FIGS. 1A-1F show results demonstrating that tamoxifen resistant breast cancer cells display ER independent survival when exposed to tamoxifen.

In this specification and the appended claims, the singular forms "a", "an", and "the" include plural references unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements, or method steps.

The terms "comprising", "comprises", and "comprised of" also encompass the term "consisting of".

The recitation of numerical ranges by endpoints includes all numbers and fractions subsumed within the respective ranges, as well as the recited endpoints.

One aspect of the technology described herein relates to a method of increasing sensitivity of estrogen receptor positive (ER⁺) breast cancer cells to treatment with an endocrine therapy. The method involves selecting ER⁺ breast cancer cells, and administering to the selected cells (i) one or more mammalian target of rapamycin (mTOR) inhibitors and (ii) one or more MAP kinase-interacting serine/threonine-protein kinase 1 (MNK1) inhibitors. The administering of (i) and (ii) to the selected cells is in an effective amount to increase the sensitivity of the ER⁺ breast cancer cells to treatment with the endocrine therapy.

The term "breast cancer" as used herein refers to a condition characterized by anomalous rapid proliferation of abnormal cells that originate in the breast of a subject. The abnormal cells often are referred to as "neoplastic cells," which as used herein refers to transformed cells that can form a solid tumor. The term "tumor" as used herein refers to an abnormal mass or population of cells (i.e., two or more cells) that result from excessive or abnormal cell division, whether malignant or benign, and pre-cancerous and cancerous cells. Malignant tumors are distinguished from benign growths or tumors in that, in addition to uncontrolled cellular proliferation, they can invade surrounding tissues and can metastasize.

The term "metastasis" or "metastasize" as used herein refers to a process in which cancer cells travel from one organ or tissue to another non-adjacent organ or tissue. Cancer cells in the breast(s) can spread to tissues and organs of a subject, and conversely, cancer cells from other organs or tissue can invade or metastasize to a breast. Cancerous cells from the breast(s) may invade or metastasize to any other organ or tissue of the body. Breast cancer cells often invade lymph node cells and/or metastasize to the liver, brain and/or bone and spread cancer in these tissues and organs. The terms "invade" or "invasion", in some embodiments, refers to the spread of cancerous cells to adjacent surrounding tissues.

In breast cancer, neoplastic cells may be identified in one or both breasts only and not in another tissue or organ, in one or both breasts and one or more adjacent tissues or organs (e.g., lymph node), or in one or both breasts and one or more non-adjacent tissues or organs to which the breast cancer cells have metastasized.

The breast cancer may be ductal carcinoma in situ, invasive ductal carcinoma (e.g., tubular carcinoma, medullary carcinoma, mucinous carcinoma, papillary carcinoma, and cribriform carcinoma), invasive lobular carcinoma, inflammatory breast cancer, lobular carcinoma in situ, or metastatic breast cancer.

Breast cancers may be classified as estrogen receptor positive or negative. Estrogen Receptor positive (ER⁺) breast cancers are cancers where active ER signaling drives proliferation. There are two major isoforms of estrogen receptor, ERα and ERβ. ERα and ERβ are encoded by two unique genes that reside on distinct chromosomes and each isoform is responsible for the regulation of a specific set of genes that elicit tissue-specific effects. The role of ERα in cancer initiation and progression has been well established in breast cancer (Fullwood et al., "An Oestrogen-Receptor-α-Bound Human Chromatin Interactome," *Nature* 462:58-64 (2009); Sommer et al., "Estrogen Receptor and Breast Cancer," *Semin. Cancer Biol.* 11:339-352 (2001); Sommer et al., "Estrogen Receptor and Breast Cancer," *Semin. Cancer Biol.* 11:339-352 (2001); Oxelmark et al., "The Cochaperone p23 Differentially Regulates Estrogen Receptor Target Genes and Promotes Tumor Cell Adhesion and Invasion," *Mol. Cell. Biol.* 26:5205-5213 (2006); and Simpson et al., "High Levels of Hsp90 Cochaperone p23 Promote Tumor Progression and Poor Prognosis in Breast Cancer by Increasing Lymph Node Metastases and Drug Resistance," *Cancer Res.* 70:8446-8456 (2010), each of which is incorporated herein by reference in its entirety).

In some embodiments of the technology described herein, the estrogen receptor positive breast cancer is ERα positive (ERα⁺) cancer. In accordance with these embodiments, the ER⁺ breast cancer cells are ERα positive (ERα⁺).

In certain embodiments, the ER⁺ breast cancer cells comprise one or more ER mutations. In some embodiments, these mutations affect the ability of the ligand binding domain to bind ligands having affinity to non-mutated ER. In certain embodiments of the technology described herein, the ER has one or more point mutations in the ligand binding domain that reduce or eliminate binding to normally binding ER ligands, and in some instances have constitutive ER signaling activity, e.g., resistant to aromatase inhibitors. In certain embodiments, the mutated ER has a ligand binding domain that is partially or completely absent. In some embodiments, the mutant receptor is a fusion receptor between a part of ERα and part or all of another protein. In some embodiments, said mutant receptor is capable of signaling through ER pathways despite not being able to bind ligand or having an attenuated affinity for ligands that bind non-mutated ER. In some embodiments, the mutant or fusion retains the ER of DNA-binding domain function.

A variety of additional molecular factors may be used to categorize ER⁺ breast cancers, including progesterone receptor and human epidermal growth factor receptor 2 (HER2) status. The ER⁺ breast cancer cells may be progesterone receptor positive (PR⁺) or progesterone receptor negative (PR⁺). The ER⁺ breast cancer cells may be human epidermal growth factor receptor 2 positive (HER2⁺) or human epidermal growth factor receptor 2 negative (HER2⁻). The ER⁺ cells may be androgen receptor positive (AR⁺) or androgen receptor negative (AR⁻).

The presence of ER (as well as other hormone receptors) in breast cancer tumor cells or tumor tissue can be readily evaluated, e.g., by immunohistochemistry (IHC). Certain embodiments of the methods disclosed herein further comprise determining that the tumor expresses ER and optionally one or more other receptors (e.g., PR, HER2, AR).

As used herein, a "mammalian target of rapamycin protein inhibitor" or "mTOR inhibitor" includes agents that inhibit (e.g., selectively inhibit) the mammalian target of rapamycin protein (mTOR). Suitable mTOR inhibitors include, but are not limited to, rapamycin (sirolimus, Rapamune®), everolimus (Affinitor® or RAD001), temsirolimus (Torisel®, CCI-779, NSC 683864), tacrolimus (FK506), ridaforolimus (AP23573, MK-8669, deforolimus), dactolisib (BEZ235, NVP-BEZ235), AZD8055, KU-0063794, sapanisertib (INK 128, MLN0128), voxtalisib (XL765, SAR245409), Torin 1, OSI-027, PF-04691502, apitolisib (GDC-0980, RG7422), GSK1059615, gedatolisib (PF-05212384, PKI-587), WYE-354, vistusertib (AZD2014), Torin 2, WYE-125132 (WYE-132), BGT226 (NVP-BGT226), WYE-687, WAY-600, Palomid 529 (P529), ETP-46464, GDC-0349, XL388, CC-115, CC-223, zotarolimus (ABT-578), GDC-0084, CZ415, SF1126, SF2523, LY3023414, MHY1485, PI-103, Torkinib (PP242), and chrysophanic acid, including solvates (e.g., hdrates) and salts thereof. Accordingly, in some embodiments according to any aspect of the technology described herein, the one or more mTOR inhibitors comprise rapamycin (sirolimus, Rapamune®), everolimus (Affinitor® or RAD001), temsirolimus (Torisel®, CCI-779, NSC 683864), tacrolimus (FK506), ridaforolimus (AP23573, MK-8669, deforolimus), dactolisib (BEZ235, NVP-BEZ235), AZD8055, KU-0063794, sapanisertib (INK 128, MLN0128), voxtalisib (XL765, SAR245409), Torin 1, OSI-027, PF-04691502, apitolisib (GDC-0980, RG7422), GSK1059615, gedatolisib (PF-05212384, PKI-587), WYE-354, vistusertib (AZD2014), Torin 2, WYE-125132 (WYE-132), BGT226 (NVP-BGT226), WYE-687, WAY-600, Palomid 529 (P529), ETP-46464, GDC-0349, XL388, CC-115, CC-223, zotarolimus (ABT-578), GDC-0084, CZ415, SF1126, SF2523, LY3023414, MHY1485, PI-103, Torkinib (PP242), chrysophanic acid, or any combination thereof.

As used herein, a "MAP kinase-interacting serine/threonine-protein kinase 1 inhibitor" or "MNK1 inhibitor" or "Mnk1 inhibitor" includes agents that inhibit (e.g., selectively inhibit) MAP kinase-interacting serine/threonine-protein kinase 1 (MNK1). Mnk1 is activated in response to treatment with growth factors, ultraviolet (UV) radiation, mitogens and stress inducing agents such as anisomycin or sorbitol as well as by cytokines such as type I and type II interferons (IFNs), tumor necrosis factor (TNF)-α, interleukin (IL)-1β, etc. (Joshi et al., "Mnk Kinase Pathway: Cellular Functions and Biological Outcomes," *World J. Biol. Chem.* 5(3):321-333), which is incorporated herein by reference in its entirety). Activated MNK1 phosphorylates the cap binding eukaryotic translation initiation factor 4E (eIF4E) at Ser209, increasing its affinity for the 7-methylguanosine-containing mRNA cap, thereby regulating protein translation. Suitable MNK1 inhibitors include, but are not limited to, BAY 1143269, CGP57380, CGP052088, ETP 45835 dihydrochloride, and eFT-508. Accordingly, in some embodiments according to any aspect of the technology described herein, the one or more MNK1 inhibitors comprises BAY 1143269, CGP 57380, CGP 052088, ETP 45835 dihydrochloride, eFT-508, or any combination thereof.

As noted above, aspects of the technology described herein relate to increasing sensitivity of ER$^+$ breast cancer cells to treatment with an endocrine therapy. As described herein, certain aspects of the technology also relate to administering one or more endocrine therapies to selected cells and/or subjects.

The term "endocrine therapy" as used herein refers to a treatment aimed at blocking the synthesis of and/or activation of a hormone. The treatment may, for example, remove the gland that synthesizes the hormone or the prohormone, block or inhibit hormone synthesis, prevent or inhibit the hormone from binding to its receptor, and/or down-regulate or degrade the hormone receptor. Endocrine therapy may be used in the treatment of breast cancer as either an adjuvant to surgery in early stage disease or as the primary treatment in more advanced stages of diseases. In some examples, endocrine therapy for ER$^+$ breast cancer may involve (but is not limited to) the use of selective estrogen receptor modulators (SERMs), aromatase inhibitors, and/or selective estrogen receptor degraders (SERDs).

As used herein, a "selective estrogen receptor modulator" or "SERM" refers to a compound that directly or indirectly competes with estrogen and modulates ER activity by changing the cofactors with which it associates. SERMs, either directly or through their active metabolites, function as estrogen receptor antagonists in breast tissue and as estrogen receptor agonists or partial agonists in the uterus, bone, and heart. SERMs can be classified based on their chemical structure as triphenylethylenes, benzothiophenes, phenylindoles, and tetrahydronaphthalenes (Patel et al., "Selective Estrogen Receptor Modulators (SERMs) and Selective Estrogen Receptor Degraders (SERDs) in Cancer Treatment," *Pharmacol. Ther.* 186:1-24 (2018), which is incorporated herein by reference in its entirety). Suitable triphenylethylene SERMs include, but are not limited to, tamoxifen (tamoxifene, Nolvadex®, Soltamox®), 4-hydroxytamoxifen, endoxifen, toremifene (Fareston®), droloxifene, and idoxifene. Suitable benzothiophene SERMs include, but are not limited to, raloxifene (Evista®), and arzoxifene. Suitable indole and tetrahydronaphthalene SERMS include, but are not limited to, bazedoxifene, pipindoxifene, and lasofoxifene.

As used herein, an "aromatase inhibitor" refers to a compound or polypeptide that directly or indirectly blocks and/or inhibits the activity of aromatase, which catalyzes an aromatization step in the synthesis of estrogen from an androgen precursor. Suitable aromatase inhibitors include, but are not limited to, anastrozole (Arimidex®), letrozole (Femara®), and exemestane (Aromasin®).

As used herein, a "selective estrogen receptor degrader" or "SERD" refers to a compound that directly or indirectly binds to and induces the degradation of the estrogen receptor, thereby inhibiting dimerization and abolishing the ER signaling pathway. Suitable SERDs include, but are not limited to, fulvestrant (Faslodex®), GW5638, GW7604, GDC810, AZD9496, and elacestrant (RAD1901) (Patel et al., "Selective Estrogen Receptor Modulators (SERMs) and Selective Estrogen Receptor Degraders (SERDs) in Cancer Treatment," *Pharmacol. Ther.* 186:1-24 (2018) and Bihani et al., "Elacestrant (RAD1901), a Selective Estrogen Receptor Degrader (SERD), Has Antitumor Activity in Multiple ER$^+$ Breast Cancer Patient-Derived Xenograft Models," *Clin. Cancer Res.* 23(16):4793-4804 (2017), each of which is incorporated herein by reference in its entirety).

In some embodiments, administering (i) one or more mTOR inhibitors and (ii) one or more MNK1 inhibitors as described herein increases the sensitivity of ER$^+$ breast cancer cells to an endocrine therapy described herein (e.g., a SERM, an aromatase inhibitor, a SERD, or any combination thereof), as compared to when the (i) one or more mTOR inhibitors and the (ii) one or more MNK1 inhibitors are not administered.

The term "sensitivity" as used in reference to increasing sensitivity of breast cancer cells to treatment with therapy (or therapies) described herein (including e.g., endocrine therapy or therapies) is a relative term which refers to an increase in the degree of effectiveness of a therapy in reducing, inhibiting, and/or suppressing growth of breast cancer cells. The term "growth" as used herein, encompasses any aspect of the growth, proliferation, and progression of breast cancer cells, including, e.g., cell division (i.e., mitosis), cell growth (e.g., increase in cell size), an increase in genetic material (e.g., prior to cell division), and metastasis. Reduction, inhibition, and/or suppression of breast cancer cell growth includes, but is not limited to, inhibition of breast cancer cell growth as compared to the growth of untreated or mock treated cells, inhibition of proliferation, inhibition of metastases, induction of breast cancer cell senescence, induction of breast cancer cell death, and reduction of breast cancer tumor size.

In some embodiments, the methods described herein increase the sensitivity of the $ER^+$ breast cancer cells to treatment with a selective estrogen receptor modulator (SERM), an aromatase inhibitor, and/or a selective estrogen receptor degrader (SERD), as compared to when the (i) one or more mTOR inhibitors and the (ii) one or more MNK1 inhibitors are not administered. In some embodiments, the method increases the sensitivity of the $ER^+$ breast cancer cells to treatment with a SERM. Suitable SERMs are described herein above. In some embodiments, the method increases the sensitivity of the $ER^+$ breast cancer cells to treatment with an aromatase inhibitor. Suitable aromatase inhibitors are described herein above. In some embodiments, the method increases the sensitivity of the $ER^+$ breast cancer cells to treatment with a SERD. Suitable SERDS are described herein above.

For example, the methods described herein may increase the sensitivity of $ER^+$ breast cancer cells to treatment with a therapy (or therapies) described herein (e.g., one or more endocrine therapies) by at least 1%, 2%, 3%, 4%, 5%, 6%, 7%, 8%, 9%, 10%, 20%, 30%, 40%, 50%, 60%, 70%, 80%, 90%, 95%, 99%, or 100%, or more, as compared to when the (i) one or more mTOR inhibitors and the (ii) one or more MNK1 inhibitors are not administered. An increase in sensitivity to a therapy may be measured by, e.g., using cell proliferation assays and/or cell cycle analysis assays.

In some embodiments, selected cells according to methods described herein exhibit resistance to treatment with an endocrine therapy prior to administering (i) one or more mTOR inhibitors and (ii) one or more MNK1 inhibitors as described herein. For example, the selected cells may exhibit resistance to treatment with a SERM, an aromatase inhibitor, and/or a SERD prior to administering (i) one or more mTOR inhibitors and (ii) one or more MNK1 inhibitors as described herein.

As used herein, the term "resistant" or "refractory" refers to a breast cancer and/or breast cancer cell that does not respond (e.g., is not sensitive) to treatment with a therapeutic agent (e.g., one or more endocrine therapies as described herein), or is less responsive than a non-resistant breast cancer cell to treatment with a therapeutic agent. As described infra, the resistance may be de novo resistance or acquired resistance.

As used herein, the term "de novo resistance" refers to resistance that exists prior to treatment with a given therapeutic agent. Therefore, de novo endocrine-resistant cancers and/or cancer cells are resistant to endocrine therapy prior to the administration of at least one treatment with the endocrine therapy.

As used herein, the term "acquired resistance" refers to resistance that is acquired after at least one treatment with a given therapeutic agent. Prior to the at least one treatment, the cancer and/or cancer cells do not possess resistance to the therapeutic agent (and, as such, the cancer and/or cancer cells are responsive and/or sensitive to the first treatment with a given agent). For example, an endocrine-resistant cancer is initially responsive or sensitive to at least one treatment with an endocrine therapy and thereafter develops a resistance to subsequent treatments with the endocrine therapy.

In certain embodiments, administering (i) one or more mTOR inhibitors and (ii) one or more MNK1 inhibitors as described herein is effective to increase endocrine therapy sensitivity to endocrine therapy resistant cells having de novo resistance or acquired resistance. In some embodiments, the methods described herein may further involve administering one or more endocrine therapies to the selected cells. Administering the one or more endocrine therapies to the selected cells may reduce growth, an invasive property, and/or a metastatic property of the selected cells. For example, administering an endocrine therapy as described herein (e.g., a SERM, aromatase inhibitor, and/or a SERD) to the selected cells may be effective to inhibit breast cancer cell growth, inhibit breast cancer cell proliferation, induce breast cancer cell senescence, and/or induce breast cancer cell death in response to treatment with an endocrine therapy described.

The method of increasing sensitivity of estrogen receptor positive ($ER^+$) breast cancer cells to treatment with an endocrine therapy can be carried out in vitro, in vivo, or ex vivo. When methods described herein are carried out in vivo, selecting $ER^+$ breast cancer cells may involve selecting a subject having $ER^+$ breast cancer and administering the (i) one or more mTOR inhibitors and the (ii) one or more MNK1 inhibitors as described herein to the selected subject.

Suitable subjects in accordance with the methods described herein include, without limitation, a mammal, e.g., a human. In certain embodiments, the selected subject is female, e.g., a premenopausal female or a postmenopausal female. In some embodiments, the subject is male. Additional suitable subjects include, but are not limited to, an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

In some embodiments, the selected subject may have acquired endocrine therapy resistance or de novo endocrine therapy resistance. In some embodiments, the selected subject exhibits resistance to treatment with an endocrine therapy prior to administering (i) one or more mTOR inhibitors and (ii) one or more MNK1 inhibitors. In some embodiments, the selected subject has been previously treated with an endocrine therapy (e.g., a SERM, aromatase inhibitor, and/or a SERD). In certain embodiments, the selected subject has progressed on prior endocrine therapy, including, without limitation, a SERD (e.g., fulvestrant), a SERM (e.g., tamoxifen), and/or an aromatase inhibitor (e.g., letrozole). For example the selected subject may have been previously treated with tamoxifen. A substantial proportion of patients with localized $ER^+$ breast cancer and all nearly with advanced disease who initially respond to tamoxifen develop de novo or acquired resistance (Early Breast Cancer Trialists' Collaborative Group, "Effects of Chemotherapy and Hormonal Therapy for Early Breast Cancer on Recurrence and 15-Year Survival: An Overview of the Randomised Trials," *Lancet* 365:1687-1717 (2005), which is hereby incorporated by reference in its entirety). In some embodiments, the selected subject may have acquired resistance or de novo resistance to tamoxifen. Accordingly, in some embodiments, the selected subject's cancer may have relapsed or progressed following tamoxifen treatment.

In some embodiments, the selected subject has not been treated for breast cancer and the (i) one or more mTOR inhibitors and (ii) one or more MNK1 inhibitors as described herein are administered, either alone (i.e., in combination with each other) or in combination with one or more additional therapeutic agents (e.g., endocrine therapies) as described herein. In some embodiments, the methods described herein further involve administering one or more endocrine therapies to the selected subject.

Another aspect of the technology described herein relates to a method of treating a subject having ER$^+$ breast cancer. The method involves selecting a subject having ER$^+$ breast cancer, where the ER$^+$ breast cancer exhibits resistance to treatment with an endocrine therapy, and administering to the selected subject (i) one or more mTOR inhibitors, (ii) one or more MNK1 inhibitors, and (iii) one or more endocrine therapies. Suitable subjects, as well as suitable mTOR inhibitors and MNK1 inhibitors are described herein.

As described herein, it has unexpectedly been found that reducing eIF4E expression or mTOR activity and also blocking MNK1 phosphorylation of eIF4E can resensitize an ER$^+$ breast cancer (e.g., an endocrine-therapy resistant or refractory cancer) to endocrine therapy. Thus, for example, administering (i) one or more mTOR inhibitors and (ii) one or more MNK1 inhibitors to a subject having ER$^+$ breast cancer, where the ER$^+$ breast cancer exhibits resistance to treatment with an endocrine therapy, restores the sensitivity of the ER$^+$ breast cancer to the/an endocrine therapy (e.g., a SERM, an aromatase inhibitor, and/or a SERD).

According to this aspect of the technology, ER$^+$ breast cancer cells in the subject may be de novo resistant or have acquired resistance to one or more endocrine therapies described herein. Accordingly, in some embodiments, breast cancer cells in the selected subject may exhibit de novo or acquired resistance to one or more endocrine therapies prior to administering the (i) one or more mTOR inhibitors and (ii) one or more MNK1 inhibitors described herein. In some embodiments, the resistance is to treatment with a SERM, an aromatase inhibitor, and/or a SERD.

As discussed above, the methods described herein may involve administering the (i) one or more mTOR inhibitors and (ii) one or more MNK1 inhibitors as described herein, either alone (i.e., in combination with each other) or in combination with one or more additional therapeutic agents (e.g., endocrine therapies and/or other additional therapeutic agents).

In some embodiments, the methods described herein involve administering one or more endocrine therapies to the selected subject. Suitable endocrine therapies include, but are not limited to, those described herein above. Additional suitable endocrine therapies as described herein include, but are not limited to, selective androgen receptor modulators (SARMs), e.g., RAD140 (testolone), 2-chloro-4-[[(1R,2R)-2-hydroxy-2-methyl-cyclopentyl]amino]-3-methyl-benzonitrile, PF-06260414, enobosarm, BMS-564929, LGD-4033, AC-262356, JNJ-28330835, S-40503, GSK-2881078, AZD-3514, MK4541, LG121071, GLPG0492, NEP28, YK11, MK0773, ACP-105, LY-2452473, S-101479, S-40542, S-42, and/or LGD-3303).

Suitable additional therapeutic agents for use in any of the methods described herein also include, but are not limited to, CDK4/6 inhibitors (e.g., palbociclib, ribociclib, trilaciclib and/or abemaciclib); PARP inhibitors (e.g., talazoparib, veliparib, niraparib, beigene290, E7449, KX01, ABT767, CK102, JPI289, KX02, IMP4297, SC10914, NT125, PJ34, VPI289 and/or ANG-3186); PIK3 inhibitors (e.g., BEZ235, GDC-0980, BKM120, GDC-0941, BYL719, GDC-0032, MK2206, GDC-0068, GSK2110183, GSK2141795, AZD5363, AZD2014, MLN0128 and/or CC-223); BCL-2 inhibitors (e.g., venetoclax, navitoclax, ABT737, G3139 and/or 555746); and MCL-1 inhibitors (e.g., 7-(5-((4-(4-(N, N-Dimethylsulfamoyl)piperazin-1-yl)phenoxy)methyl)-1,3-dimethyl-1H-pyrazol-4-yl)-1-(2-morpholinoethyl)-3-(3-(naphthalen-1-yloxy)propyl)-1H-indole-2-carboxylic Acid, 563845, omacataxine, seliciclib, UMI-77, AT101, sabutoclax and/or TW-37).

In practicing this and other aspects of the present application that involve administering combination(s) of therapeutic agents to a subject (e.g., the one or more mTOR inhibitors, the one or more MNK1 inhibitors, and/or one or more additional therapeutic agents described herein), the combination(s) of therapeutic agents are administered in combination to a subject in need. The phrase "in combination" means that the therapeutic agents described herein may be administered before, during, or after the administration of any, some, or all of the other therapeutic agents described herein.

For example, the (i) one or more mTOR inhibitors and the (ii) one or more MNK1 inhibitors can be administered about one week apart, about 6 days apart, about 5 days apart, about 4 days apart, about 3 days apart, about 2 days apart, about 24 hours apart, about 23 hours apart, about 22 hours apart, about 21 hours apart, about 20 hours apart, about 19 hours apart, about 18 hours apart, about 17 hours apart, about 16 hours apart, about 15 hours apart, about 14 hours apart, about 13 hours apart, about 12 hours apart, about 11 hours apart, about 10 hours apart, about 9 hours apart, about 8 hours apart, about 7 hours apart, about 6 hours apart, about 5 hours apart, about 4 hours apart, about 3 hours apart, about 2 hours apart, about 1 hour apart, about 55 minutes apart, about 50 minutes apart, about 45 minutes apart, about 40 minutes apart, about 35 minutes apart, about 30 minutes apart, about 25 minutes apart, about 20 minutes apart, about 15 minutes apart, about 10 minutes apart, or about 5 minutes apart. In certain embodiments the one or more mTOR and one or more MNK1 inhibitors are administered to the subject simultaneously or substantially simultaneously. In certain of these embodiments, the (i) one or more mTOR inhibitors and the (ii) one or more MNK1 inhibitors disclosed herein may be administered as part of a single formulation. Included are kits where (i) one or more mTOR and (ii) one or more MNK1 inhibitors described herein are contained within a kit together, for example as a copackaging arrangement.

As another non-limiting example, the (i) one or more mTOR inhibitors and/or (ii) the one or more MNK1 inhibitors (on the one hand) and one or more additional therapeutic agents (e.g., one or more endocrine therapies and/or other additional therapeutic agents) (on the other hand) can be administered about one week apart, about 6 days apart, about 5 days apart, about 4 days apart, about 3 days apart, about 2 days apart, about 24 hours apart, about 23 hours apart, about 22 hours apart, about 21 hours apart, about 20 hours apart, about 19 hours apart, about 18 hours apart, about 17 hours apart, about 16 hours apart, about 15 hours apart, about 14 hours apart, about 13 hours apart, about 12 hours apart, about 11 hours apart, about 10 hours apart, about 9 hours apart, about 8 hours apart, about 7 hours apart, about 6 hours apart, about 5 hours apart, about 4 hours apart, about 3 hours apart, about 2 hours apart, about 1 hour apart, about 55 minutes apart, about 50 minutes apart, about 45 minutes apart, about 40 minutes apart, about 35 minutes apart, about 30 minutes apart, about 25 minutes apart, about 20 minutes apart, about 15 minutes apart, about 10 minutes apart, or about 5 minutes apart. In certain embodiments (i) one or more mTOR inhibitors, (ii) one or more MNK1 inhibitors, and/or (iii) one or more additional therapeutic agents (e.g., the one or more endocrine therapies and/or other additional therapeutic agents described herein) are administered to the subject simultaneously or substantially simultaneously. In certain of these embodiments, (i) one or more mTOR inhibitors, (ii) one or more MNK1 inhibitors, and/or (iii) one or more additional therapeutic agents disclosed herein (e.g., the one or more endocrine therapies and/or other additional therapeutic agents described herein) may be administered as part of a single formulation. Included are kits where (i) one or more mTOR inhibitors, (ii) one or more MNK1 inhibitors, and (iii) one or more additional therapeutic agents (e.g., the one or more endocrine therapies and/or other additional therapeutic agents described herein) are contained within a kit together, for example as a copackaging arrangement.

Also contemplated herein is any variation of the above with respect to the sequence of administering (i) one or more mTOR inhibitors, (ii) one or more MNK1 inhibitors, and (iii) one or more additional therapeutic agents in combination.

The therapeutic agents and combinations for use in the methods described herein can be formulated according to any available conventional method. Examples of preferred dosage forms include a tablet, a powder, a subtle granule, a granule, a coated tablet, a capsule, a syrup, a troche, an inhalant, a suppository, an injectable, an ointment, an ophthalmic ointment, an eye drop, a nasal drop, an ear drop, a cataplasm, a lotion and the like. In the formulation, generally used additives such as a diluent, a binder, an disintegrant, a lubricant, a colorant, a flavoring agent, and if necessary, a stabilizer, an emulsifier, an absorption enhancer, a surfactant, a pH adjuster, an antiseptic, an antioxidant and the like can be used. In addition, the formulation is also carried out by combining compositions that are generally used as a raw material for pharmaceutical formulation, according to conventional methods. Examples of these compositions include, for example, (1) an oil such as a soybean oil, a beef tallow and synthetic glyceride; (2) hydrocarbon such as liquid paraffin, squalane and solid paraffin; (3) ester oil such as octyldodecyl myristic acid and isopropyl myristic acid; (4) higher alcohol such as cetostearyl alcohol and behenyl alcohol; (5) a silicon resin; (6) a silicon oil; (7) a surfactant such as polyoxyethylene fatty acid ester, sorbitan fatty acid ester, glycerin fatty acid ester, polyoxyethylene sorbitan fatty acid ester, a solid polyoxyethylene castor oil and polyoxyethylene polyoxypropylene block co-polymer; (8) water soluble macromolecule such as hydroxyethyl cellulose, polyacrylic acid, carboxyvinyl polymer, polyethyleneglycol, polyvinylpyrrolidone and methylcellulose; (9) lower alcohol such as ethanol and isopropanol; (10) multivalent alcohol such as glycerin, propyleneglycol, dipropyleneglycol and sorbitol; (11) a sugar such as glucose and cane sugar; (12) an inorganic powder such as anhydrous silicic acid, aluminum magnesium silicicate and aluminum silicate; (13) purified water, and the like.

Additives for use in the above formulations may include, for example, (1) lactose, corn starch, sucrose, glucose, mannitol, sorbitol, crystalline cellulose and silicon dioxide as the diluent; (2) polyvinyl alcohol, polyvinyl ether, methyl cellulose, ethyl cellulose, gum arabic, tragacanth, gelatine, shellac, hydroxypropyl cellulose, hydroxypropylmethyl cellulose, polyvinylpyrrolidone, polypropylene glycol-polyoxyethylene-block co-polymer, meglumine, calcium citrate, dextrin, pectin and the like as the binder; (3) starch, agar, gelatine powder, crystalline cellulose, calcium carbonate, sodium bicarbonate, calcium citrate, dextrin, pectic, carboxymethylcellulose/calcium and the like as the disintegrant; (4) magnesium stearate, talc, polyethyleneglycol, silica, condensed plant oil and the like as the lubricant; (5) any colorants whose addition is pharmaceutically acceptable is adequate as the colorant; (6) cocoa powder, menthol, aromatizer, peppermint oil, cinnamon powder as the flavoring agent; (7) antioxidants whose addition is pharmaceutically accepted such as ascorbic acid or alpha-tophenol.

The therapeutic agents and combinations for use in the methods described herein can be formulated into a pharmaceutical composition as any one or more of the active compounds described herein and a physiologically acceptable carrier (also referred to as a pharmaceutically acceptable carrier or solution or diluent). Such carriers and solutions include pharmaceutically acceptable salts and solvates of compounds used in the methods described herein, and mixtures comprising two or more of such compounds, pharmaceutically acceptable salts of the compounds and pharmaceutically acceptable solvates of the compounds. Such compositions are prepared in accordance with acceptable pharmaceutical procedures such as described in Remington: The Science and Practice of Pharmacy, 20th edition, ed. Alfonso R. Gennaro (2000), which is incorporated herein by reference in its entirety.

The term "pharmaceutically acceptable carrier" refers to a carrier that does not cause an allergic reaction or other untoward effect in patients to whom it is administered and are compatible with the other ingredients in the formulation. Pharmaceutically acceptable carriers include, for example, pharmaceutical diluents, excipients or carriers suitably selected with respect to the intended form of administration, and consistent with conventional pharmaceutical practices. For example, solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof. Pharmaceutically acceptable carriers may further comprise minor amounts of auxiliary substances such as wetting or emulsifying agents, preservatives or buffers, which enhance the shelf life or effectiveness of the therapeutic agent.

Reference to therapeutic agents described herein includes any analog, derivative, isomer, metabolite, pharmaceutically acceptable salt, pharmaceutical product, hydrate, N-oxide, crystal, polymorph, prodrug or any combination thereof.

The therapeutic agents in a free form can be converted into a salt, if need be, by conventional methods. The term "salt" used herein is not limited as long as the salt is pharmacologically acceptable; preferred examples of salts include a hydrohalide salt (for instance, hydrochloride, hydrobromide, hydroiodide and the like), an inorganic acid salt (for instance, sulfate, nitrate, perchlorate, phosphate, carbonate, bicarbonate and the like), an organic carboxylate salt (for instance, acetate salt, maleate salt, tartrate salt, fumarate salt, citrate salt and the like), an organic sulfonate salt (for instance, methanesulfonate salt, ethanesulfonate salt, benzenesulfonate salt, toluenesulfonate salt, camphorsulfonate salt and the like), an amino acid salt (for instance, aspartate salt, glutamate salt and the like), a quaternary ammonium salt, an alkaline metal salt (for instance, sodium salt, potassium salt and the like), an alkaline earth metal salt (magnesium salt, calcium salt and the like) and the like. In addition, hydrochloride salt, sulfate salt, methanesulfonate salt, acetate salt and the like are preferred as "pharmacologically acceptable salt" of the compounds disclosed herein.

In certain embodiments, the therapeutic agents disclosed herein may be in a prodrug form, meaning that it must undergo some alteration (e.g., oxidation or hydrolysis) to achieve its active form.

By way of example, suitable modes of systemic administration of the therapeutic agents and/or combinations disclosed herein include, without limitation, orally, topically, transdermally, parenterally, intradermally, intrapulmonary, intramuscularly, intraperitoneally, intravenously, subcutaneously, or by intranasal instillation, by intracavitary or intravesical instillation, intraocularly, intraarterialy, intralesionally, or by application to mucous membranes. In certain embodiments, the therapeutic agents of the methods described herein are delivered orally.

Suitable modes of local administration of the therapeutic agents and/or combinations disclosed herein include, without limitation, catheterization, implantation, direct injection, dermal/transdermal application, or portal vein administration to relevant tissues, or by any other local administration technique, method or procedure generally known in the art. The mode of affecting delivery of agent will vary depending on the type of therapeutic agent and the cancer to be treated.

A therapeutically effective amount of a combination of therapeutic agents (e.g., one or more mTOR inhibitor(s), one or more MNK1 inhibitor(s), and optionally one or more additional therapeutic agents) in the methods disclosed herein is an amount that, when administered over a particular time interval, results in achievement of one or more therapeutic benchmarks (e.g., slowing or halting of tumor growth, resulting in tumor regression, cessation of symptoms, etc.). The combination for use in the presently disclosed methods may be administered to a subject one time or multiple times. In those embodiments where the compounds are administered multiple times, they may be administered at a set interval, e.g., daily, every other day, weekly, or monthly. Alternatively, they can be administered at an irregular interval, for example on an as-needed basis based on symptoms, patient health, and the like. For example, a therapeutically effective amount of a combination may be administered once a day (q.d.) for one day, at least 2 days, at least 3 days, at least 4 days, at least 5 days, at least 6 days, at least 7 days, at least 10 days, or at least 15 days. Optionally, the status of the cancer or the regression of the tumor is monitored during or after the treatment, for example, by a FES-PET scan of the subject. The dosage of the combination administered to the subject can be increased or decreased depending on the status of the cancer or the regression of the tumor detected.

The skilled artisan can readily determine this amount, on either an individual subject basis (e.g., the amount of a compound necessary to achieve a particular therapeutic benchmark in the subject being treated) or a population basis (e.g., the amount of a compound necessary to achieve a particular therapeutic benchmark in the average subject from a given population). Ideally, the therapeutically effective amount does not exceed the maximum tolerated dosage at which 50% or more of treated subjects experience nausea, hirsutism, voice hoarsening or other more serious reactions that prevent further drug administrations.

For example, a dose of between 0.01 μg/kg of body weight and 0.5 g/kg of body weight of an inhibitor of a MNK1 inhibitor or an mTOR inhibitor may be used in in the methods of the present invention.

A therapeutically effective amount may vary for a subject depending on a variety of factors, including variety and extent of the symptoms, sex, age, body weight, or general health of the subject, administration mode and salt or solvate type, variation in susceptibility to the drug, the specific type of the disease, and the like. One means of demonstrating acute response to the present treatment regimens is to analyze the sensitivity of $ER^+$ breast cancer cells or tumors to treatment with one or more endocrine therapies. It has been discovered that the combination of one or more mTOR inhibitor(s) and one or more MNK1 inhibitor(s) used in the present methods lead to sensitization of $ER^+$ breast cancer to endocrine therapies, indicating a response to the therapeutic agents.

The effectiveness of the methods of the present application in increasing sensitivity to treatment with an endocrine therapy may be evaluated, for example, by assessing changes in tumor burden and/or disease progression following treatment with the one or more therapeutic agents described herein according to the Response Evaluation Criteria in Solid Tumours (Eisenhauer et al., "New Response Evaluation Criteria in Solid Tumours: Revised RECIST Guideline (Version 1.1)," *Eur. J. Cancer* 45(2): 228-247 (2009), which is hereby incorporated by reference in its entirety). In some embodiments, tumor burden and/or disease progression is evaluated using imaging techniques including, e.g., X-ray, computed tomography (CT) scan, magnetic resonance imaging, mammography, and/or ultrasound (Eisenhauer et al., "New Response Evaluation Criteria in Solid Tumours: Revised RECIST Guideline (Version 1.1)," *Eur. J. Cancer* 45(2): 228-247 (2009), which is hereby incorporated by reference in its entirety). Tumor burden and/or disease progression may be monitored prior to, during, and/or following treatment with one or more of the therapeutic agents described herein.

In some embodiments, the response to treatment with the methods described herein results in at least about 1%, 2%, 3%, 4%, 5%, 6%, 7%, 8%, 9%, 10%, 20%, 30%, 40%, 50%, 60%, 70%, 80%, 90%, 95%, 99%, or 100% decrease in tumor size as compared to baseline tumor size. Thus, the response to treatment with any of the methods described herein may be partial (e.g., at least a 30% decrease in tumor size, as compared to baseline tumor size) or complete (elimination of the tumor).

In some embodiments, the effectiveness of the methods described herein may be evaluated, for example, by assessing endocrine therapy induced apoptosis and/or cell cycle progression in $ER^+$ breast cancer cells following treatment with the (i) one or more mTOR inhibitors and the (ii) one or more MNK1 inhibitors as described herein.

In some embodiments, the methods described herein may be effective to inhibit disease progression, inhibit tumor growth, reduce primary tumor size, relieve tumor-related symptoms, inhibit tumor-secreted factors (e.g., tumor-secreted hormones), delay the appearance of primary or secondary $ER^+$ breast cancer tumors, slow development of primary or secondary $ER^+$ breast cancer tumors, decrease the occurrence of primary or secondary $ER^+$ breast cancer tumors, slow or decrease the severity of secondary effects of disease, arrest tumor growth, and/or achieve regression of $ER^+$ breast cancer tumors in a selected subject. Thus, the methods described herein are effective to increase the therapeutic benefit to the selected subject.

In some embodiments, the methods described herein reduce the rate of tumor growth in the selected subject by at least about 1%, 2%, 3%, 4%, 5%, 6%, 7%, 8%, 9%, 10%, 20%, 30%, 40%, 50%, 60%, 70%, 80%, 90%, 95%, 99%, or more.

In certain embodiments, the methods described herein reduce the rate of tumor invasiveness in the selected subject by at least about 1%, 2%, 3%, 4%, 5%, 6%, 7%, 8%, 9%, 10%, 20%, 30%, 40%, 50%, 60%, 70%, 80%, 90%, 95%, 99%, or more.

In specific embodiments, the methods described herein reduce the rate of tumor progression in the selected subject by at least about 1%, 2%, 3%, 4%, 5%, 6%, 7%, 8%, 9%, 10%, 20%, 30%, 40%, 50%, 60%, 70%, 80%, 90%, 95%, 99%, or more.

In various embodiments, the methods described herein reduce the rate of tumor recurrence in the selected subject by at least about 1%, 2%, 3%, 4%, 5%, 6%, 7%, 8%, 9%, 10%, 20%, 30%, 40%, 50%, 60%, 70%, 80%, 90%, 95%, 99%, or more.

In some embodiments, the methods described herein reduce the rate of metastasis in the selected subject by at least about 1%, 2%, 3%, 4%, 5%, 6%, 7%, 8%, 9%, 10%, 20%, 30%, 40%, 50%, 60%, 70%, 80%, 90%, 95%, 99%, or more.

In some embodiments, a therapeutically effective amount may include an amount which alters the level of a biomarker. As used herein, the term "biomarker" may refer to a substance used as an indicator of a process, event, or condition. A biomarker can be a biomolecule such as a nucleic acid molecule (e.g., microRNA, genomic DNA, etc.), a protein, a polysaccharide, and the like. Biomarkers include tumor antigens and tumor markers. In one embodiment, a biomarker indicates the presence of cancer, e.g., breast cancer. In one embodiment, a biomarker may be used to determine the efficacy of treatment.

In one embodiment, a biomarker may be used to determine the progression of a condition, e.g., breast cancer.

The MUC-1 associated antigen, or CA 27.29, is a cancer antigen highly associated with breast cancer. As used herein, the term "CA27.29 biomarker" refers to a biomarker for breast cancer. In one embodiment, CA27.29 is a biomarker for advanced breast cancer.

"PSA (prostate-specific antigen) biomarker" is used as a biomarker for prostate cancer, however PSA was also found in the blood of women with breast cancer at higher levels compared to women without breast cancer. PSA is useful also as a biomarker for breast cancer.

"CTX biomarker" and "NTX biomarker" are the C-telopeptide and N-telopeptide of collagen type I, respectively, which are used as biomarkers of bone turnover. NTX and CTX biomarkers may be sensitive indicators of the presence of bone metastases in breast cancer patients.

"Cancer Antigen (CA) 15-3 biomarker" is used as a biomarker of breast cancer, as well as pancreatic, lung, ovarian, colon, and liver cancers.

"Carcinoembryonic Antigen (CEA) biomarker" is used as a biomarker of certain malignancies, including, colorectal, gastrointestinal, lung, and breast cancers.

In some embodiments, a method of the present application lowers CA27.29 biomarker levels is a subject. In certain embodiments, a method of the present application lowers PSA in a subject. In certain embodiments, the methods described herein lower CTX biomarker in a subject. In certain embodiments, a method of the present application lowers NTX biomarker in a subject. In certain embodiments, a method of the application lowers the level of CA15-3 biomarker in a subject. In certain embodiments, a method of the present application lowers the level of CEA biomarker in a subject.

In certain embodiments, a method of the present application maintains the level of CA27.29 in a subject. In certain embodiments, a method of the present application maintains the level of PSA in a subject. In certain embodiments, a method of the present application maintains the level of CTX biomarker in a subject. In certain embodiments, a method of the present application maintains the level of NTX biomarker. In certain embodiments, a method of the application maintains the level of CA15-3 biomarker in a subject. In ceratin embodiments, a method of the present application maintains the level of CEA biomarker in a subject.

In some embodiments, two or more of the therapeutic agents described herein are combined in a kit. Accordingly, another aspect of the technology described herein is a kit useful for treating breast cancer (e.g., ER⁺ breast cancer) comprising one or more mTOR inhibitors, one or more MNK1 inhibitors, and, optionally, one or more additional therapeutic agents as described herein above.

EXAMPLES

The following examples are provided to illustrate embodiments of the present invention but are by no means intended to limit its scope.

Materials and Methods for Examples 1-5

Chemicals and Inhibitors: Final concentrations of chemicals and inhibitors used were 0.02% DMSO, 1 µM 4-OHT (Millipore), 20 nM RAD001 (Selleck Chemicals), and 10 µM CGP57380 (Sigma).

Cell Lines and Cell Culture: MCF7 and BR7 cells were maintained in improved MEM (IMEM) with L-glutamine without phenol red (Cellgro), 5% fetal bovine serum (FBS) (Gibco), 0.4% gentamicin sulfate (Lonza), 0.5 µg/mL fungizone (Gibco), and 5 µg/mL plasmocin at 37° C. in a 5% $CO_2$ tissue culture incubator. 4-OHT (1 µM) was added to TamR cells every 72 hours. HEK293FT cells were maintained in DMEM with L-glutamine (Corning), 10% FBS, 1% penicillin-streptomycin (Life Technologies), 1 mM sodium pyruvate (Thermo Scientific), and 1% MEM non-essential amino acids (Thermo Scientific). Cells were routinely checked for mycoplasma contamination.

Patient Cohorts and Tissues: Archival tumor tissue specimens were obtained with prior Institutional Review Board (IRB) approval for patients ≥18 years of age with ER⁺ (≥5% ER⁺ staining) invasive ductal breast cancer (IDC) stage II/III treated with adjuvant tamoxifen and/or aromatase inhibitor (Table 1 and Table 2). Patients who recurred within 5 years were considered resistant. A pathology database of all available treated tumor specimens was queried to identify cases between 2002 and 2011 that had a clinical description of <5-year recurrence or no recurrence at 10 years.

TABLE 1

Biomarkers of eIF4E and mTOR Activity in Tamoxifen Sensitive and Resistant ER⁺ Breast Cancer

| | | Recurrent (n = 14) | Not Recurrent (n = 10) | 0/1+ vs 2+/3+ |
|---|---|---|---|---|
| P-eIF4E | 0 | 0 | 0 | |
| | 1+ | 0 | 3 (42.8%) | |
| | 2+ | 0 | 1 (14.4%) | |
| | 3+ | 10 (100%) | 3 (42.8%) | 0.050 |

TABLE 1-continued

Biomarkers of eIF4E and mTOR Activity in Tamoxifen Sensitive and Resistant ER+ Breast Cancer

|  |  | Recurrent (n = 14) | Not Recurrent (n = 10) | 0/1+ vs 2+/3+ |
|---|---|---|---|---|
| P-4E-BP1 | 0 | 0 | 1 (14.3%) |  |
|  | 1+ | 3 (30.0%) | 4 (57.1%) |  |
|  | 2+ | 5 (50.0%) | 2 (28.6%) |  |
|  | 3+ | 2 (20%) | 0 | 0.153 |
| Total eIF4E | 0 | 0 | 1 (14.3%) |  |
|  | 1+ | 0 | 0 |  |
|  | 2+ | 0 | 1 (14.3%) |  |
|  | 3+ | 10 (100%) | 5 (71.4%) | 0.412 |

IHC was performed for total and S209 (MNK) phosphorylated levels of eIF4E, and mTORC1 target phosphorylation of P-rS6 and P-4E-BP1.

TABLE 2

Biomarkers of eIF4E and mTOR Activity in Tamoxifen or Aromatase Sensitive and Resistant ER+ Breast Cancer

|  |  | Recurrent (n = 23) | Not Recurrent (n = 16) | 0/1+ vs 2+/3+ |
|---|---|---|---|---|
| P-eIF4E | 0 | 0 | 0 |  |
|  | 1+ | 0 | 4 (36.4%) |  |
|  | 2+ | 2 (11.8%) | 2 (18.2%) |  |
|  | 3+ | 15 (88.2%) | 5 (45.4%) | 0.016 |
| P-4E-BP1 | 0 | 0 | 1 (9.1%) |  |
|  | 1+ | 6 (37.5%) | 5 (45.5%) |  |
|  | 2+ | 6 (37.5%) | 4 (36.3%) |  |
|  | 3+ | 4 (25.0%) | 1 (9.1%) | 0.452 |
| Total eIF4E | 0 | 0 | 1 (9.1%) |  |
|  | 1+ | 0 | 1 (9.1%) |  |
|  | 2+ | 0 | 0 |  |
|  | 3+ | 17 (100%) | 9 (81.8%) | 0.146 |

IHC was performed for total and S209 (MNK) phosphorylated levels of eIF4E, and mTORC1 target phosphorylation of rpS6 and 4E-BP1.

Anchorage-Dependent Colony Formation Assays: Cells were trypsinized, filtered, and counted using an automated cell counter (Bio-Rad). Cells ($1 \times 10^3$) were seeded in triplicate in six-well culture dishes using IMEM supplemented with 5% charcoal-stripped FBS and 0.4% gentamicin sulfate and allowed to adhere overnight. The medium was changed, and the indicated treatments were carried out. The medium and treatments were changed every 72 hours for 10-12 days. Colonies were washed, fixed, and stained with 0.5% Crystal Violet in 6% glutaraldehyde. Colonies containing ≥50 cells were scored.

Cell Cycle Analysis: Cells were trypsinized, filtered, and counted using an automated cell counter (Bio-Rad). Cells ($7 \times 10^5$) were seeded on 10-cm culture plates in IMEM (Corning) with 5% FBS (Gibco) and 0.4% gentamicin sulfate (Lonza) and allowed to adhere overnight. The medium was changed to IMEM (Corning) with 1% charcoal-stripped FBS (HyClone) and 0.4% gentamicin sulfate for 48 hours. Cells were treated with the appropriate drug for 72 hours and with fresh drug after 48 hours. Cells were trypsinized and fixed in 70% ethanol overnight at 4° C. Cells were washed with PBS and treated with 0.5 mg/mL RNase A for 30 minutes at 37° C. Cells were washed again with PBS and stained with 50 μg/mL propidium iodide (PI) or Hoechst 33342 for 45 minutes at room temperature and protected from light. Data were collected using a FACScalibur or LSRII UV and analyzed with FlowJo 10.0.

Polysome Associated mRNA Isolation: Isolation of ribosome-bound mRNA by polysome separation was performed as described previously with minor modifications (Silvera et al., "mTORC1 and -2 Coordinate Transcriptional and Translational Reprogramming in Resistance to DNA Damage and Replicative Stress in Breast Cancer Cells," *Mol. Cell. Biol.* 37:e00577-16 (2017), which is incorporated herein by reference in its entirety). Briefly, MCF7 cells were seeded 48 hours prior to treatment, and cells were treated with 100 μg/mL cycloheximide for 10 minutes at 37° C., trypsinized, and collected in ice-cold PBS containing protease inhibitor cocktail and EDTA-free (Roche Di-agnostics). All subsequent steps contained 100 μg/mL cycloheximide. Cells were resuspended in low-salt buffer (LSB; 20 mM Tris at pH 7.4-7.5, 10 mM NaCl, 3 mM $MgCl_2$, ribonuclease inhibitor (Thermo Scientific)) and incubated for 3-5 minutes on ice. Detergent buffer (LSB with 1.2% Triton X-100, 0.2 M sucrose) was then added, and cells were lysed with 15-20 strokes in a sterilized Dounce homogenizer at 4° C. Lysates were cleared by microfuge centrifugation at maximum speed for 5 minutes, and supernatant was combined with 100 μL of heparin buffer (LSB with 10 mg/mL heparin, 1.5 M NaCl) and then layered on a 15%-50% sucrose gradient in LSB using equal $OD_{260}$ units of samples. Gradients were centrifuged at 36,000 rpm for 2 hours in a SW40Ti rotor (Beckman Coulter), and polysome profiles were done at UV absorbance 254 nm by continuous flow cell monitoring and collected using an Isco UA-6 absorbance detector (Teledyne ISCO) and with a Foxy R1 fraction collector (Teledyne ISCO) at 1.5 mL/minute.

RNA-Seq and Analysis: RNA was extracted and purified from pooled polysome fractions using the RNeasy minikit (Qiagen) as per the manufacturer's instructions. RNA quality was measured by a Bioanalyzer (Agilent Technologies). Fractions containing two to three bound ribosomes were considered poorly translated (light fractions), and those containing four or more bound ribosomes were considered well translated (heavy fraction). RNA-seq was carried out by the New York University School of Medicine Genome Technology Core using the Illumina HiSeq 2500 single read. To quantify translational efficiency, the difference in $log_2$ intensity between matched polysomal mRNA and total mRNA was determined. To examine differences in transcription and translation, total mRNA and polysome mRNA were quantile-normalized separately. Statistical analysis was performed using the limma R package (Ritchie et al., "Limma Powers Differential Expression Analyses for RNA-Sequencing and Microarray Studies," *Nucleic Acids Res.* 43:e47 (2015), which is incorporated herein by reference in its entirety). Gene enrichment analysis was performed using IPA software, and GO analysis was performed using the DAVID online tool.

Quantitative Real-Time PCR (RT-qPCR) and Analysis: RNA was extracted using Trizol as per the manufacturer's instructions. One microgram of RNA was used for reverse transcription reaction using Promega GoScript, as per the manufacturer's instructions. qRT-PCR was completed using iTaq Universal 2× SYBR Green qPCR master mix (Bio-Rad) and an Applied Biosystems 7500 Fast RT-PCR machine as per the manufacturers' instructions. Fold change was calculated using the $2^{-\Delta\Delta Ct}$ method.

Cap Chromatography: In brief, cells were lysed in NP-40 buffer (50 mM HEPES at pH7.0, 150 mM NaCl, 2 mM EDTA, 25 mM NaF, 25 mM β-glycerophosphate, 2 mM $Na_3VO_4$, 1% IGEPAL, Complete miniprotease inhibitor cocktail tablet±EDTA (Roche)), and lysates were cleared by microcentrifugation at 13,000 rpm for 10 minutes at 4° C. Lysate protein concentration was determined by BCA assay, equal amounts were incubated with $m^7GTP$ Sepharose beads for 1 hour at 4° C., and beads were collected by centrifugation, washed three times with lysis buffer, resolved by 10% or 12% SDS-PAGE, and transferred to a PVDF transfer membrane (Millipore). The membrane was blocked in 5% BSA in TBS-T at 4° C. Primary antibodies were incubated overnight at 4° C. Secondary ECL antibodies (GE Healthcare) were incubated for 1 hour at room temperature in 5% reconstituted dried milk in TBS-T. Protein was imaged using the chemiluminescence method and Gene-mate autoradiography film.

Cell Proliferation Assay: Cell proliferation was measured using the CellTiter 96 nonradioactive cell proliferation assay kit (Promega) according to the manufacturer's instructions. MCF7 cells were plated at 1500 cells per well in triplicate in 96-well culture plates. Cells were allowed to attach overnight. On day 0, 15 µL of dye solution containing tetrazolium was added to each well and incubated for 4 hours at 37° C. One-hundred microliters of Stop Six was added to each well to solubilize the formazan products using the overnight method in a humidified chamber. Absorbance was measured at 570 nm. Four more time points were collected on days 1-4. Time points were normalized to day 0.

Statistical analysis: Unpaired t-test and two-way or one-way ANOVA were used for biological studies when applicable to determine statistical significance. Biomarkers were of ordinal measurements and used Fisher's exact test. Data were analyzed using GraphPad Prism 6.0e. Significant values were considered $P<0.05$ (*), $P<0.01$ (), or $P<0.001$ (*).

Immunoblot Studies: In brief, cells were lysed in NP-40 buffer (50 mM HEPES, pH 7.0, 150 mM NaCl, 2 mM EDTA, 25 mM NaF, 25 mM β-glycerophosphate, 2 mM $Na_3VO_4$, 1% IGEPAL, and Complete Mini protease inhibitor cocktail tablet+/−EDTA; Roche) or RIPA lysis buffer (1% Triton X-100, 1% sodium deoxycholate, 0.1% SDS, 150 mM NaCl, 50 mM Tris, pH 7.4, 2 mM $Na_3VO_4$, 25 mM β-glycerophosphate, 15 mM NaF, and complete protease inhibitor mix; Roche) and lysate cleared by centrifugation at 13,000 rpm for 10 minutes at 4° C. Lysate protein concentration was determined for each sample using BCA assay. Equal amounts of lysate resolved by 10 or 12% SDS-PAGE and transferred to a PVDF transfer membrane. Membrane was blocked in 5% BSA in TBS-T at 4° C. Primary antibodies were incubated at 4° C. overnight. Secondary ECL antibodies (GE Healthcare) were incubated for 1 hour at RT in 5% Milk in TBS-T. Protein was imaged using chemiluminescence method and Genemate autoradiography film. The following antibody dilutions were used: mouse anti-eIF4E (BD Bioscience #610270, 1:5000), rabbit anti-P-eIF4E S209 (Abcam #ab76256, 1:10000), rabbit anti-eEF2 (Cell Signaling #2332, 1:1000), rabbit anti-β-actin (Cell Signaling #4967, 1:1000), rabbit anti-4E-BP1 (Cell Signaling #9644, 1:1000), rabbit polyclonal anti-eIF4G1 (1:1000), rabbit anti-eIF4A (Cell Signaling #2013, 1:5000), rabbit anti-P-eIF4E-BP1 S65 (Cell Signaling #9451, 1:1000), rabbit anti-S6 ribosomal protein (Cell Signaling #2217, 1:5000), rabbit anti-Akt (Cell Signaling #9272, 1:1000), rabbit anti-P-S6 ribosomal protein S235/236 (Cell Signaling #2211, 1:7000), rabbit anti-mTOR (Cell Signaling #2983, 1:1000), rabbit anti-TSC2 (Cell Signaling #3612, 1:1000), rabbit anti-eIF4B (Cell Signaling #3592, 1:1000), mouse anti-PABP (Abcam #ab6125, 1:1000), rabbit anti-eIF2a (Cell Signaling #9722, 1:1000), rabbit anti-eIF3H (Cell Signaling #3413, 1:1000), rabbit anti-eIF6 (Cell Signaling #3833, 1:1000), mouse anti-Runx2 (Millipore #05-1478, 1:1000), and rabbit anti-β-tubulin (Cell Signaling #2146, 1:1000). Quantitation was performed by determination of the integrated density of the bands using ImageJ software.

$^{35}$S-Methionine Metabolic Protein Labeling: Global protein synthesis was measured as previously described (Ramirez-Valle et al., "eIF4GI Links Nutrient Sensing by mTOR to Cell Proliferation and Inhibition of Autophagy," *J. Cell Biol.* 181(2):293-307 (2008), which is incorporated herein by reference in its entirety). Cells ($2\times10^5$) were seeded, in triplicate, into 6-well culture plates and allowed to adhere for 48-72 hours. Cells were labeled with 25 µCi $^{35}$S-methionine/cysteine protein labeling mix (PerkinElmer) for 30 minutes at 37° C. using DMEM without L-Methionine or L-Cysteine supplemented with 5% FBS. Cells were lysed in NP-40 buffer (50 mM HEPES, pH 7.0, 150 mM NaCl, 2 mM EDTA, 25 mM NaF, 25 mM β-glycerophosphate, 2 mM $Na_3VO_4$, 0.5% IGEPAL, and complete protease inhibitor tablet; Thermo Scientific). Lysates were cleared by centrifugation at maximum speed for 15 minutes at 4° C. Proteins were precipitated in 10% TCA followed by scintillation counting. Protein concentration was measured by the BCA assay (Thermo Scientific). For studies involving doxycycline treatment, Dox was added 48 hours after plating and maintained throughout the course of the study.

pTripz Construct Expression: The tetracycline responsive element (TRE) was induced using 1-2 µg/ml of doxycycline was administered to cells for 48-96 hours. When possible, RFP expression was analyzed through fluorescent microscopy or FACS analysis.

Generation of Inducible Constructs: shRNA cassettes were cloned into 5'-XhoI and 3'-EcoRI sites of Inducible TRIPZ vector (pTripz). Constructs were transformed into One Shot Stbl3 cells (Invitrogen) and grown on LB-amp/zeo plates overnight at 37° C. Plasmids were purified from individual colonies and sequenced. Sequencing primer: (5'-GGAAAGAATCAAGGAGG-3'; SEQ ID NO:1). Overexpression constructs were generated following a similar method except the ORFs were cloned into 5'-AgeI and 3'-MluI sites and sequenced with the following primers: Fwd: (5'-CGAGGTTCTAGACGAGTTTA-3'; SEQ ID NO:2); Rev: (5'-GCCTTAAGAACCCCAGTATCAG-3'; SEQ ID NO:3). The shRNA cassette sequences are as follows: eIF4E-1 (5'-CACAATAGTCAGAAAACAACT-3'; SEQ ID NO:4), eIF4E-2 (5'-GCGTCAAGCAATCGAGATTTG-3'; SEQ ID NO:5), TSC2 (5'-CAGCATTAATCTCTTACCATA-3'; SEQ ID NO:6) and Runx2 (5'-CCACAGAATTTGCATTTAGAG-3'; SEQ ID NO:7). The eIF4E and 4E-BP1 ORFs were subcloned from the pBABE-puro retrovirus vector using the AgeI/MluI cloning sites. Point mutations were made using site-directed mutagenesis (Agilent Technologies).

Generation of Stable Cells Lines: HEK293FT cells were transfected with pTripz lentivirus vector, psPAX2, and PMD2.G using lipofectamine 2000 (Life Technology) for 6-8 hours. Media was changed to DMEM (Corning) supplemented with 5% heat-inactivated FBS (Gibco). Virus was collected 48 and 72 hours after transfection. Virus was concentrated and either used immediately to transduce MCF7 cells or stored at −80° C. Cells were infected in the presence of Polybrene (5-10 µg/ml) and thereafter selected for resistance to puromycin (Sigma) or geneticin (Gibco) for up to one week.

Immunohistochemistry (IHC) and Scoring: All kits and developing substrates were obtained from Vector Laboratories. Paraffin-embedded tumor sections (4 µm thickness) were de-paraffinized in xylene and ethanol, rehydrated and subjected to antigen retrieval by microwaving for 30 minutes in antigen unmasking solution (Vector Laboratories), then 5% $H_2O_2$ to block endogenous peroxidase activity for 30 minutes at room temperature followed by protein blocking of non-specific epitopes with 1.5% normal horse serum (Vector Laboratories). Slides were incubated with primary antibodies for 4E-BP1 and P-4E-BP1 (S65, Cell Signaling), P-eIF4E (S209, Abcam), S6 and P-S6 (S240/244, Cell Signaling), and eIF4E (BD Transduction) overnight at 4° C. After washing with PBS-T, slides were incubated with secondary antibody for 2 hours at room temperature and DAB staining carried out according to manufacturer instructions (Vectastain ABC kit, Vector Laboratories). Slides were counterstained with hematoxylin. Specimens were analyzed by a pathologist blinded to the study and 20% of specimens chosen at random spot scored by a second pathologist also blinded to the study. Specimens were scored as 0, 1, 2, 3+with a cut-off for staining that had to include at least 5% of the cells in a given population and took into consideration the percentage of positive cells as follows. For quartile scoring: 0<5%; +1≥6% but <33%; +2>33% but <65%; +3>66%. For tertile staining: 0<5%; +1≥6% but <50%; +2≥50%.

Figures 2A, 2B, 2C, 2D, 2E, 2F:
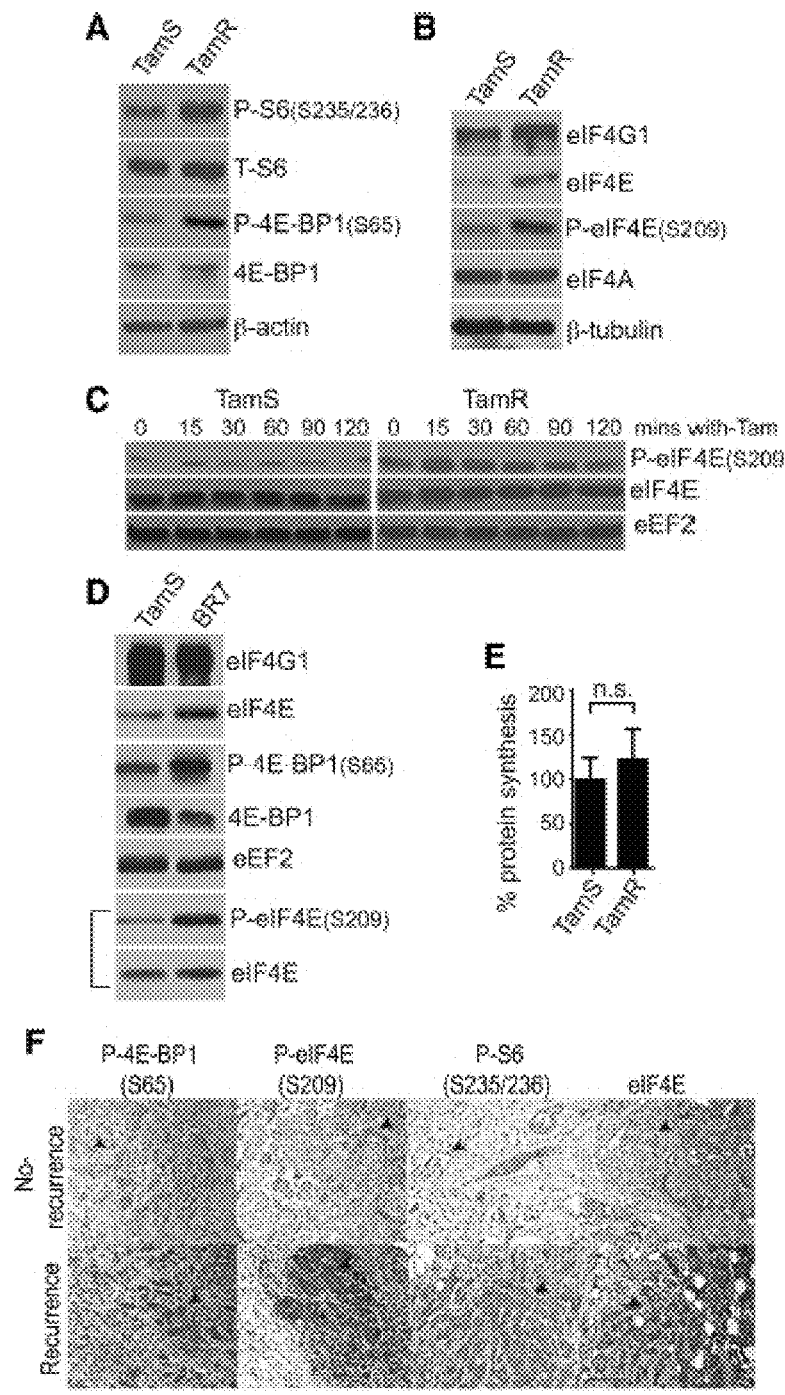
FIGS. 2A-2F show results demonstrating mTORC1 and MAPK pathway hyperactivation in tamoxifen resistance in ER+ breast cancer.
Figures 3A, 3B, 3C, 3D, 3E, 3F, 3G:
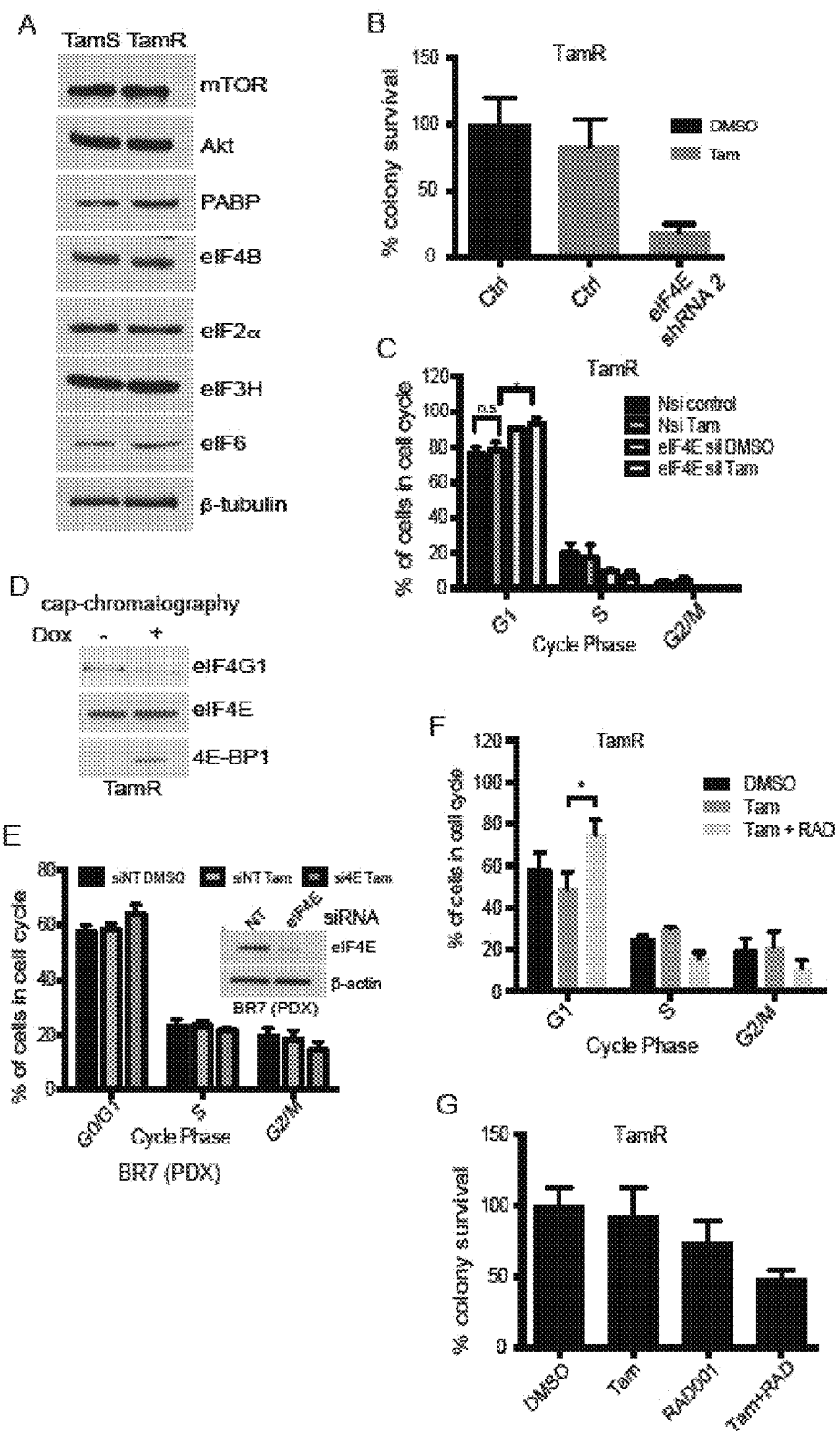
FIGS. 3A-3G show results demonstrating that the selective therapeutic inhibition of mTORC1 can restore tamoxifen sensitivity to ER+ breast cancer cells.

Example 1—Increased eIF4E Abundance, eIF4E S209 Phosphorylation, and mTORC1 and MNK Activity in Tamoxifen-Resistant Breast Cancers and Cell Lines Established MCF7 tamoxifen-responsive LCC1 cells (referred to herein as TamS cells) and isotype-matched tamoxifen-resistant LCC9 cells (referred to herein as TamR cells) used widely as a clinically relevant model of tamoxifen therapy resistance (e.g., Brunner et al., "MCF7/LCC9: An Antiestrogen-Resistant MCF-7 Variant in Which Acquired Resistance to the Steroidal Antiestrogen ICI 182,780 Confers an Early Cross-Resistance to the Nonsteroidal Antiestrogen Tamoxifen," *Cancer Res.* 57:3486-3493 (1997); Clarke et al., "Antiestrogen Resistance in Breast Cancer and the Role of Estrogen Receptor Signaling," *Oncogene* 22:7316-7339 (2003); and Howell et al., "The Use of Selective Estrogen Receptor Modulators and Selective Estrogen Receptor Down-Regulators in Breast Cancer," *Best Pract. Res. Clin. Endocrinol. Metab.* 18:47-66 (2004), each of which is incorporated herein by reference in its entirety) were characterized. Tamoxifen-sensitive cells demonstrate impaired growth and fail to transition through $G_1$ to S phase during treatment (Brunner et al., "MCF7/LCC9: An Antiestrogen-Resistant MCF-7 Variant in Which Acquired Resistance to the Steroidal Antiestrogen ICI 182,780 Confers an Early Cross-Resistance to the Nonsteroidal Antiestrogen Tamoxifen," *Cancer Res.* 57:3486-3493 (1997), each of which is hereby incorporated by reference in its entirety), consistent with the primary inhibitory effect of tamoxifen. TamR cells are resistant to inhibition and maintain normal proliferation and survival to clinically relevant doses of tamoxifen (FIGS. 1A-1C). An ER$^+$ tamoxifen-resistant patient-derived xenograft (PDX) known as BR7 was also insensitive to tamoxifen, as shown by normal cell cycle distribution despite tamoxifen treatment (FIG. 1D). TamR and BR7 cells were insensitive to tamoxifen-induced repression of canonical ER signaling as well, in contrast to TamS cells (FIGS. 1E-1F). mTORC1 activity, measured by phosphorylation of 4E-BP1 (S65) and ribosomal protein S6, was elevated in TamR compared with TamS cells (FIG. 2A), as were eIF4E levels (FIG. 2B) and eIF4E phosphorylation (FIG. 2C, normalized for eIF4E levels). eIF4E levels and S209 phosphorylation were also increased in BR7 (PDX) cells compared with TamS cells (FIG. 2D). Therefore, increased mTORC1 and MNK pathway activity is associated with endocrine resistance in cell lines and in a PDX model of endocrine-resistant disease. Increased levels of eIF4E do not typically increase overall protein synthesis very strongly, which was also observed here (FIG. 2E). However, increased levels of eIF4E can selectively increase the translation of specific mRNAs in different physiological conditions (Avdulov et al., "Activation of Translation Complex eIF4F is Essential for the Genesis and Maintenance of the Malignant Phenotype in Human Mammary Epithelial Cells," *Cancer Cell* 5:553-563 (2004); Holcik et al., "Translation Mechanism and Regulation: Old Players, New Concepts. Meeting on Translational Control and Non-Coding RNA," *EMBO Rep.* 8:639-643 (2007); Pelletier et al., "Targeting the eIF4F Translation Initiation Complex: A Critical Nexus for Cancer Development," *Cancer Res.* 75:250-263 (2015); and Truitt et al., "Differential Requirements for eIF4E Dose in Normal Development and Cancer," *Cell* 162:59-71 (2015), each of which is incorporated herein by reference in its entirety). Importantly, there were no significant differences in the levels of other key translation factors in TamR compared with TamS cells, apart from the increased expression of eIF4E (FIG. 3A).

Biopsy specimens from ER$^+$ invasive intraductal breast cancer patients who progressed on treatment (de novo resistance) or recurred within 5 years of tamoxifen treatment, a standard for resistance, were investigated compared with nonrecurrent treated tumors at 10 years. Despite the small sample size (due to difficulty in obtaining well-validated resistant and sensitive tumor specimens), tamoxifen-resistant tumors showed significantly increased eIF4E S209 phosphorylation (Mnk1 activation) compared with tamoxifen-sensitive tumors (Table 1, P=0.05), as did tamoxifen- or aromatase-resistant tumors (P=0.016) (Table 2). Given the fact that mTORC1 is already highly active and that eIF4E is already overexpressed as a driver of breast cancer, it is not surprising that there was only a trend toward increased mTORC1 activity (P-4E-BP1) and slightly increased eIF4E levels with tamoxifen or aromatase resistance that did not reach statistical significance. The lower saturation level of immunohistochemistry compared with immunoblot may also contribute to the smaller detectable increase in eIF4E levels, although it was apparent in many of the specimens (FIG. 2F).

Figures 4A, 4B, 4C, 4D, 4E, 4F, 4G:
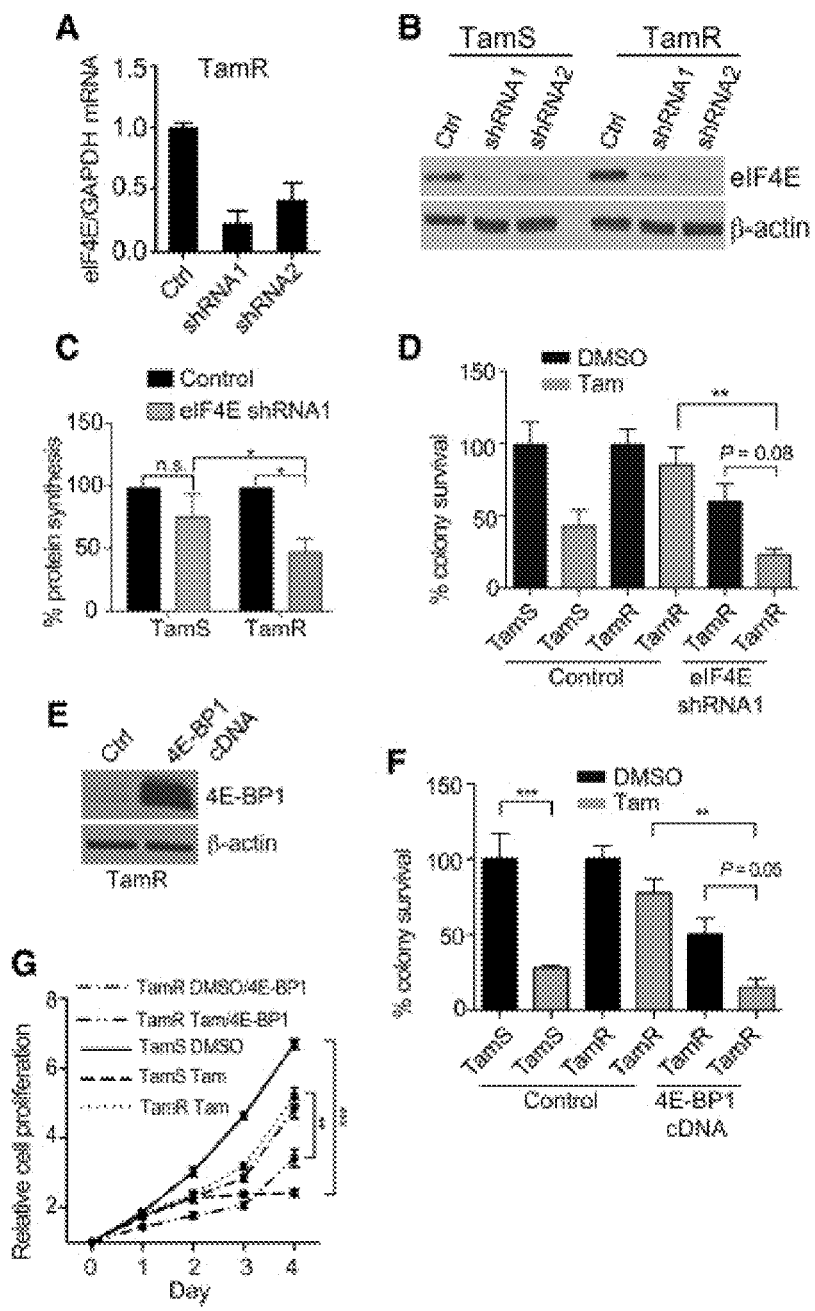
FIGS. 4A-4G show results demonstrating that blocking eIF4F complex formation by targeting eIF4E partially restores tamoxifen sensitivity.

Example 2—Reduced Overexpression of eIF4E and its S209 Phosphorylation are Required to Restore Tamoxifen Sensitivity to Resistant Cells The role of eIF4E-selective mRNA translation in endocrine therapy resistance was tested by stably transducing TamS and TamR cells with doxycycline (Dox)-inducible shRNAs targeting the 3' UTR of eIF4E. Quantitative RT-PCR (qRT-PCR) and immunoblot analysis showed an average fourfold reduction of eIF4E mRNA and protein levels (FIGS. 4A-2B). Interestingly, whereas levels of eIF4E silencing were similar in both cell lines, it resulted in a larger (50% greater) reduction in overall protein synthesis only in TamR cells, indicating a moderate addiction to elevated levels of eIF4E with the acquisition of tamoxifen resistance (FIG. 4C).

Whether the increased expression and/or phosphorylation of eIF4E is essential for selective mRNA translation and tamoxifen resistance was investigated. Silencing eIF4E in the presence of 4-hydroxytamoxifen (4-OHT), the active metabolite of tamoxifen, reduced clonogenic cell survival and cell growth of TamR cells by fourfold compared with the nonsilencing control and threefold to fourfold compared with silenced but untreated TamR cells (FIG. 4D; FIGS.

3B-3C). Similarly inducible overexpression of 4E-BP1 in TamR-resistant cells (FIG. 4E) reduced eIF4E cap-binding complexes (FIG. 3D) and resulted in a fourfold reduction in cell proliferation and survival of tamoxifen-treated TamR cells compared with controls (FIGS. 4F-4G). Moreover, silencing eIF4E in the BR7 PDX model restored tamoxifen sensitivity, as shown by delayed cell cycling in response to treatment (FIG. 3E). Everolimus (RAD001) is an inhibitor of the mTORC1 signaling pathway and is currently approved for the treatment of hormone receptor-positive endocrine therapy-resistant breast cancers. To confirm the involvement of mTORC1 in endocrine resistance, TamR cells were treated with RAD001, which partially resensitized them to tamoxifen, as shown by the restoration of inhibition of cell proliferation and decreased survival (FIGS. 3F-3G). Both increased mTORC1 activity and eIF4E availability are therefore required for tamoxifen resistance. Collectively, these data suggest a critical role for the eIF4E/4E-BP1 balance in regulating tamoxifen resistance and responsiveness by mTORC1 activity.

Figures 5A, 5B, 5C, 5D, 5E:
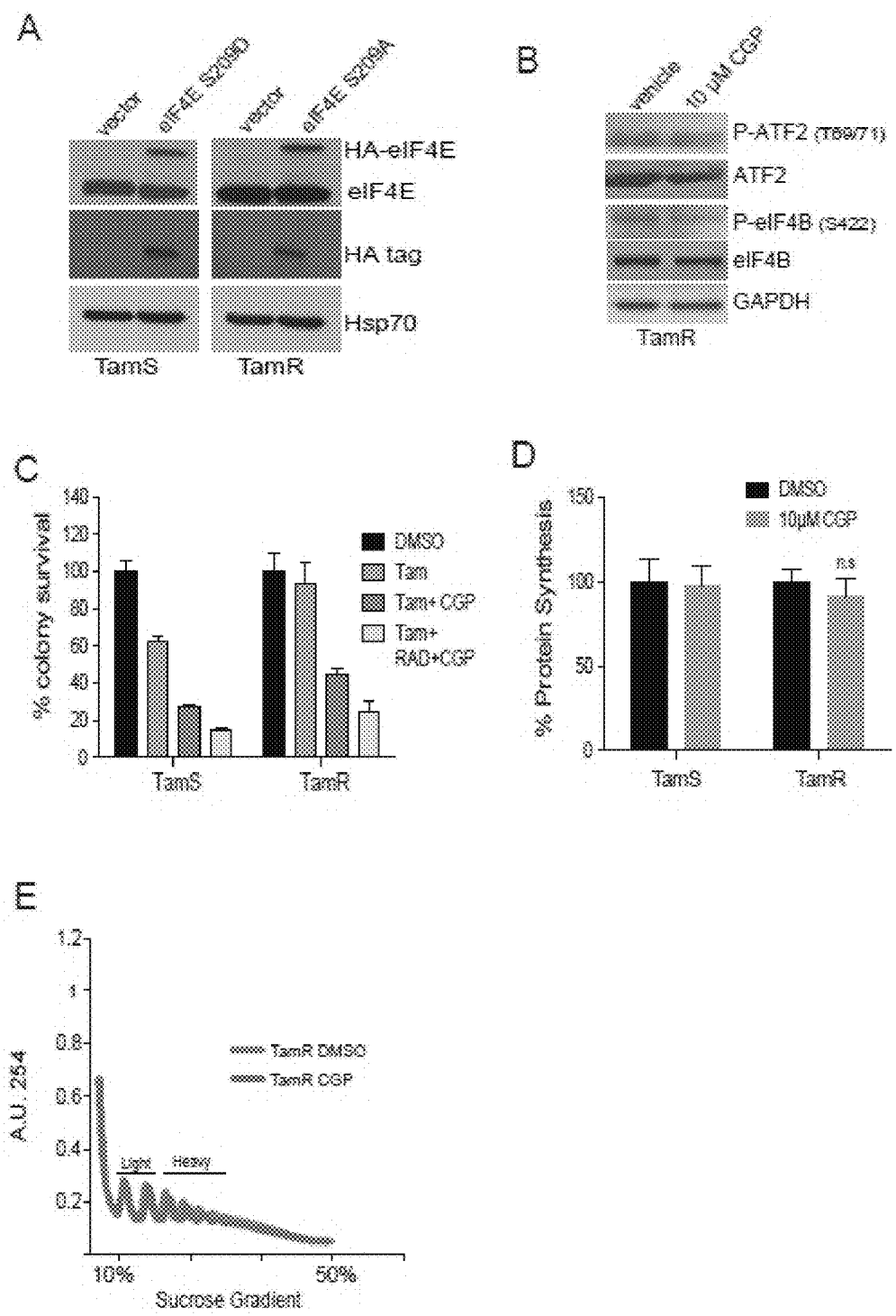
FIGS. 5A-5E show results demonstrating that eIF4E 5209 phosphorylation promotes drug resistance via selective mRNA translation.
Figures 6A, 6B, 6C, 6D, 6E, 6F:
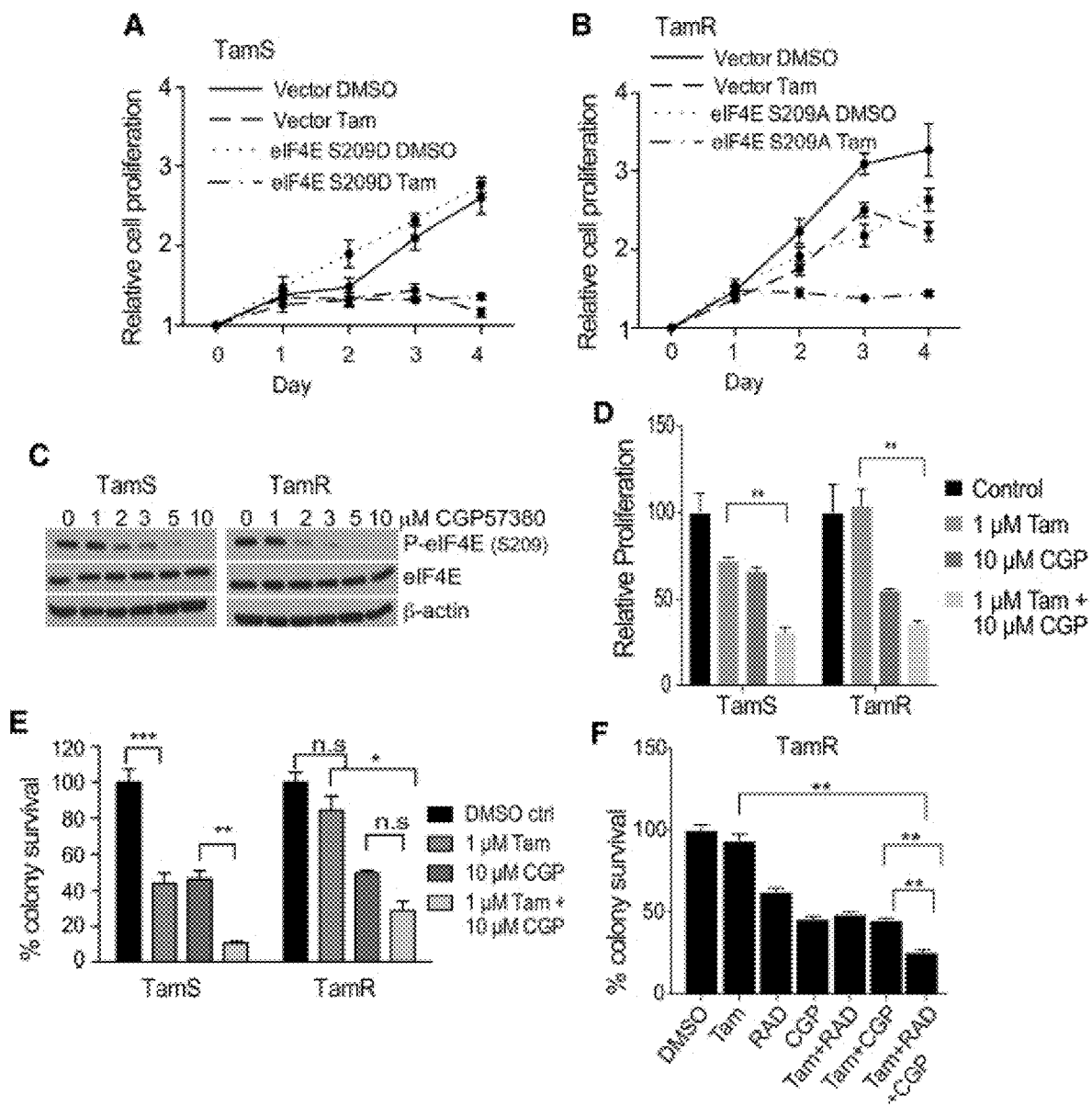
FIGS. 6A-6F show results demonstrating that eIF4E 5209 phosphorylation promotes tamoxifen resistance.

A requirement for eIF4E 5209 phosphorylation (MNK1-mediated) has been implicated in tumorigenesis and metastasis (Bianchini et al., "Phosphorylation of eIF4E by MNKs Supports Protein Synthesis, Cell Cycle Progression and Proliferation in Prostate Cancer Cells," *Carcinogenesis* 29:2279-2288 (2008); Wheater et al., "The Role of MNK Proteins and eIF4E Phosphorylation in Breast Cancer Cell Proliferation and Survival," *Cancer Biol. Ther.* 10:728-735 (2010); and Robichaud et al., "Phosphorylation of eIF4E Promotes EMT and Metastasis via Translational Control of SNAIL and MMP-3," *Oncogene* 34:2032-2042 (2015), each of which is incorporated herein by reference in its entirety), and increased eIF4E S209 phosphorylation was observed in tamoxifen-resistant breast tumor tissues and cell lines. Therefore, the role of eIF4E phosphorylation in tamoxifen resistance was examined. A serine-to-alanine HA-tagged eIF4E protein (S209A) or a serine-to-aspartic acid protein (S209D) was expressed in TamS and TamR cells (FIG. 5A). Endogenous eIF4E was silenced to eliminate its contribution, and cells were assayed for proliferation in the presence or absence of 4-OHT (FIGS. 6A-6B). Notably, TamR cells were blocked in proliferation by expression of the non-phosphorylated S209A eIF4E mutant only in the presence of tamoxifen (implicating an essential role for MNK1-mediated eIF4E phosphorylation at S209) and overexpression of eIF4E in tamoxifen resistance. However, expression of the S209D phosphomimetic eIF4E protein in TamS cells did not confer tamoxifen-resistant proliferation. These data suggest two possibilities: that acquisition of tamoxifen resistance is multigenic and not solely the result of eIF4E overexpression and phosphorylation (whereas resistance can be reversed by impairing either because both are important) and/or that the phospho-mimetic eIF4E variant protein cannot fully recapitulate the effects of eIF4E phosphorylation, consistent with a previous report (Topisirovic et al., "Phosphorylation of the Eukaryotic Translation Initiation Factor eIF4E Contributes to its Transformation and mRNA Transport Activities," *Cancer Res.* 64:8639-8642 (2004), which is incorporated herein by reference in its entirety).

The effect of inhibition of MNK1 on tamoxifen sensitivity by the small molecule MNK1 inhibitor CGP57380 was next investigated. Dose escalation studies on both TamS and TamR cells established a concentration of 10 μM for complete inhibition of eIF4E phosphorylation by CGP57380 (FIG. 6C), where it has no inhibitory activity on other families of related kinases (p38, JNK1, and RSKs) (Knauf et al., "Negative Regulation of Protein Translation by Mitogen-Activated Protein Kinase-Interacting Kinases 1 and 2," *Mol. Cell. Biol.* 21:5500-5511 (2001) and Rowlett et al., "MNK Kinases Regulate Multiple TLR Pathways and Innate Proinflammatory Cytokines in Macrophages," *Am. J. Physiol. Gastrointest. Liver Physiol.* 294:G452-G459 (2008), each of which is incorporated herein by reference in its entirety). This was confirmed in TamR cells by examining ATF2 phosphorylation at Thr69/71 (a target of RSK, JNK1, and p38 MAPK) and eIF4B S422 (a target of RSKs)—the next most sensitive kinases of CGP57380 inhibition. There was no change in phosphorylation of either protein with treatment (FIG. 5B). Combined treatment with tamoxifen and CGP57380 significantly resensitized TamR cells to tamoxifen, as shown by a >60% reduction in proliferation and clonogenic survival compared with untreated controls (FIGS. 6D-6E). As described previously, cotreatment with mTORC1 inhibitor RAD001 produced a further additive reduction in cell survival (FIG. 6F; FIG. 5C), with only a 10% reduction in global protein synthesis despite complete ablation of eIF4E phosphorylation (FIG. 5D). Polysome profiling of tamoxifen-resistant cells following CGP57380 treatment showed no significant differences (FIG. 5E), suggesting a role for eIF4E phosphorylation in selectively reprogramming the translation of a small subset of mRNAs involved in tamoxifen resistance.

Figures 7A, 7B, 7C, 7D, 7E, 7F:
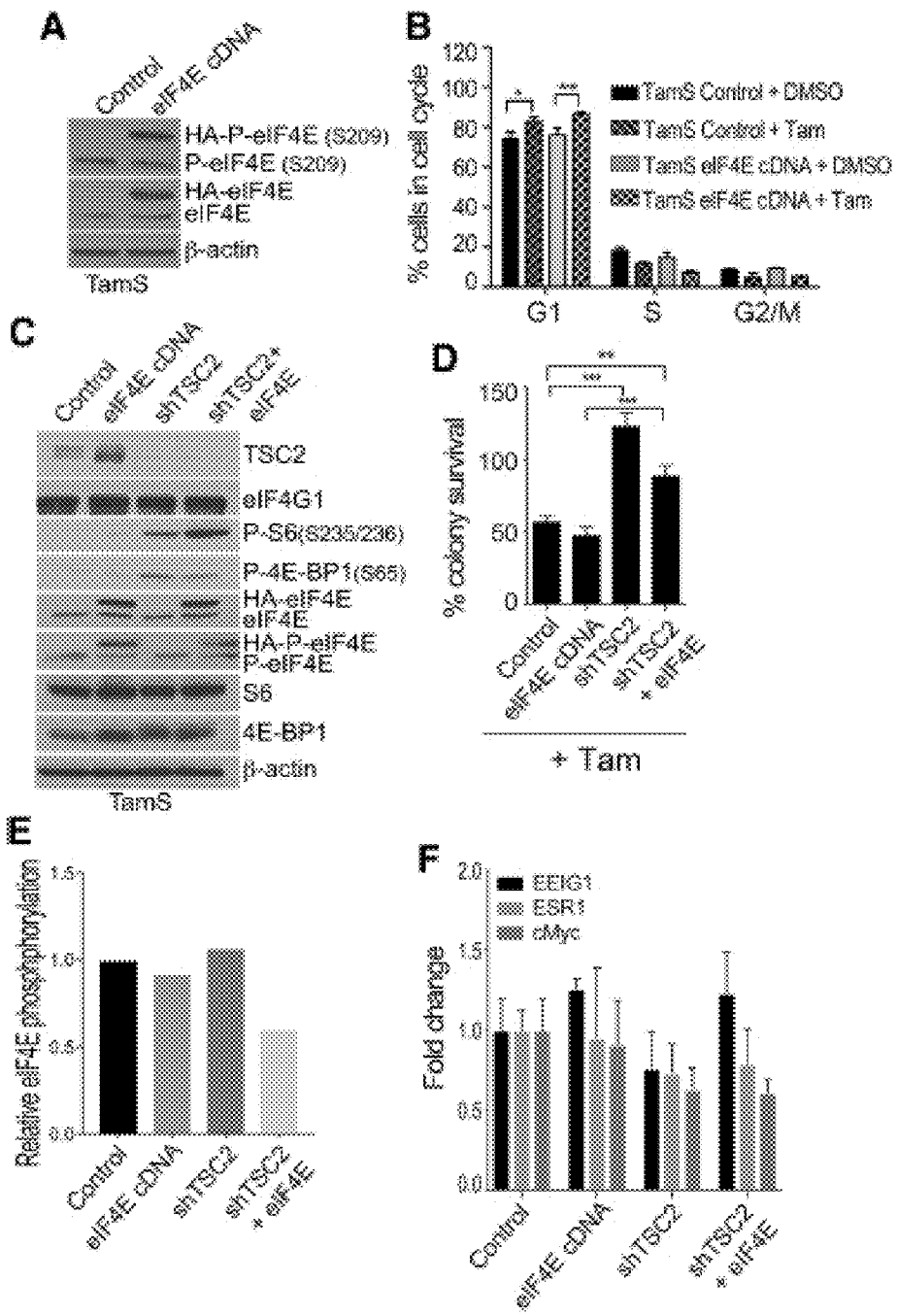
FIGS. 7A-7F show results demonstrating that hyperactivation of mTORC1 and eIF4E overexpression reprogram the cancer genome to mimic tamoxifen resistance.

Example 3—Both Overexpression of eIF4E and its Phosphorylation are Required to Promote Tamoxifen Resistance in Normally Sensitive ER$^+$ Breast Cancer Cells Since merely expressing a phospho-mimetic eIF4E is insufficient to confer tamoxifen resistance to normally sensitive cells, whether both overexpression of eIF4E and increased eIF4E S209 phosphorylation were required was evaluated. TamS cells were stably transfected with a Dox-inducible HA-tagged eIF4E cDNA that tripled eIF4E levels (FIG. 7A). Tamoxifen-sensitive TamS cells were unable to proliferate in the presence of tamoxifen regardless of eIF4E overexpression (FIG. 7B). However, since eIF4E availability and phosphorylation are limited by 4E-BP1, mTORC1 was hyperactivated by disrupting the repressing TSC1/TSC2 complex through shRNA silencing of Tsc2 (FIG. 7C). Silencing Tsc2 strongly increases mTORC1 signaling (Sato et al., "Rapamycin Reverses Impaired Social Interaction in Mouse Models of Tuberous Sclerosis Complex," *Nat. Commun.* 3:1292 (2012), which is incorporated herein by reference in its entirety), demonstrated by increased phosphorylation of 4E-BP1 and ribosomal protein S6. Importantly, Tsc2 silencing conferred tamoxifen resistance to normally sensitive ER$^+$ breast cancer cells (FIG. 7D). Cosilencing Tsc2 and overexpressing eIF4E slightly reduced tamoxifen resistance for unknown reasons but might be related to homeostatic regulation of eIF4E levels. A somewhat lower level of eIF4E and 4E-BP1 phosphorylation in Tsc2 silenced eIF4E-overexpressing cells was observed, consistent with this possibility. The importance of eIF4E S209 phosphorylation using a phospho-dead protein could not be tested due to the inability to sufficiently silence endogenous eIF4E in cells that were already drug-selected twice. Nevertheless, eIF4E and its phosphorylation, increased mTORC1 activity, and increased levels of available eIF4E and its phosphorylation can confer tamoxifen resistance. Somewhat less eIF4E and 4E-BP1 phosphorylation was noted in Tsc2 silenced cells with eIF4E overexpression, supportive of this possibility (FIG. 7C). There was no change in basal ER signaling under these conditions, as shown by induction of ER biomarker mRNAs (FIG. 7E).

Figures 8A, 8B, 8C, 8D, 8E, 8F, 8G:
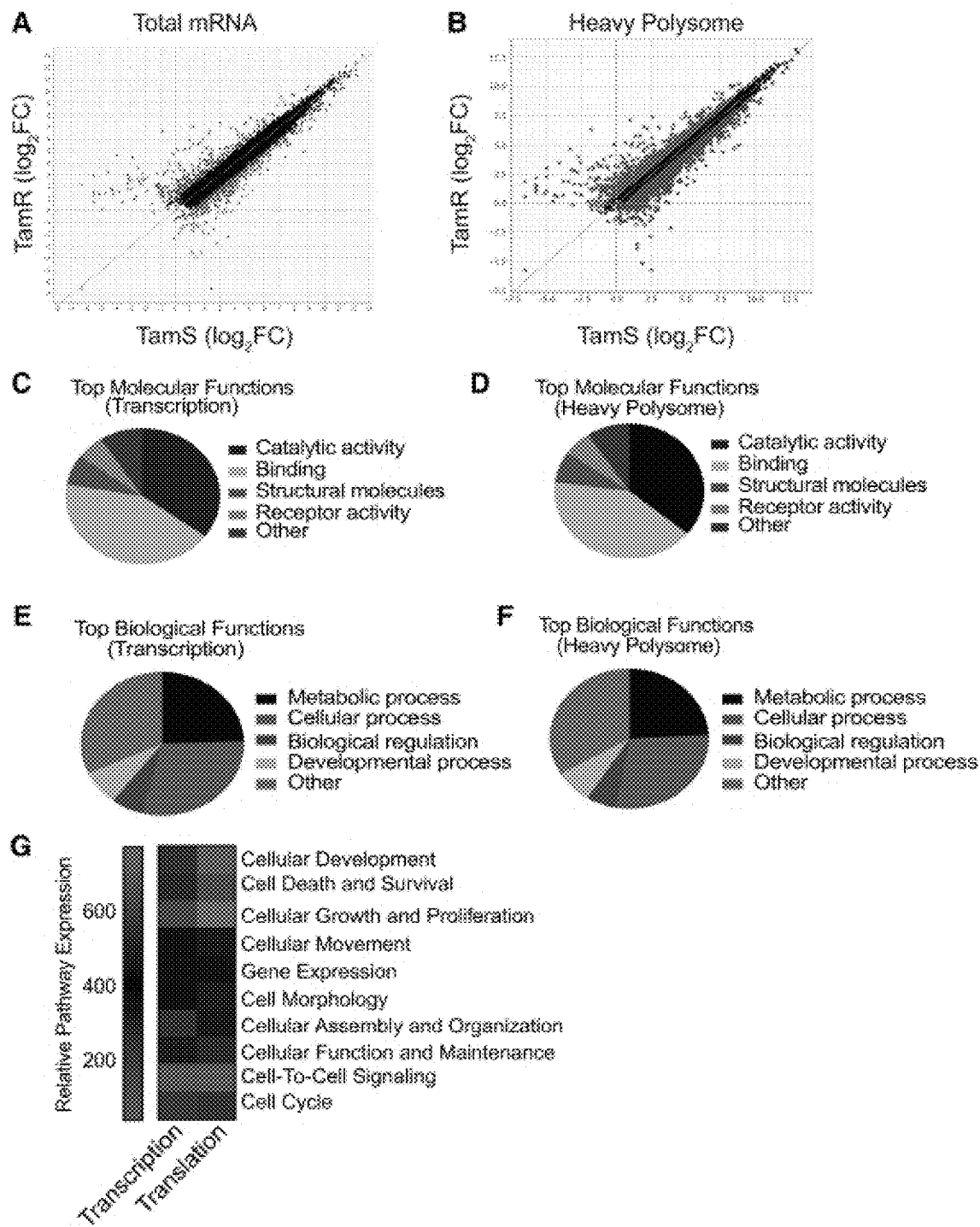
FIGS. 8A-8G show results demonstrating the selective translation of mRNAs important in cell proliferation, survival, and genomic reprogramming in tamoxifen-resistant compared with tamoxifen-sensitive breast cancer cells.

Example 4—mRNAs are Altered in Abundance and Translation in Tamoxifen-Resistant Compared with Tamoxifen-Sensitive Breast Cancer Cells Research on tamoxifen-resistant disease has not yet been focused on differential mRNA translation. mRNAs that are selectively altered in translation in tamoxifen-resistant cells were identified by conducting a genome-wide translatome and transcriptome analysis using RNA sequencing (RNA-seq) of TamR and TamS cells. Three sets of conditions were analyzed to fully represent the genome-wide changes in mRNA abundance and translation: (1) expression levels for total mRNA (transcription), (2) changes in translation (heavy polysome fraction) regardless of mRNA abundance or translational regulation, and (3) translation-specific changes (ratio of heavy polysome mRNA/total mRNA) (FIGS. 8A-8B; Table 3). Analyses used a cutoff of $\log_2$ 1.0 (2-fold) for total mRNA and $\log_2$ 0.6 (1.5-fold) for heavy polysome association; the latter was set lower because smaller changes in protein expression can have significant physiological effects.

Significance was set at P<0.05 for both mRNA and polysome analysis. Gene ontology (GO) analyses of significantly altered genes in both transcription and translation revealed an enrichment of developmental, cell survival, and differentiation pathways in endocrine therapy-resistant cells (FIGS. 8C-8G). Specific enrichment in up-regulated Hox and DNA recombination genes was observed, with a concomitant repression of estrogen and Tgfβ genes (Table 4). Moreover, Hox genes encode transcription factors that specify stem cell fate determination and are also important in oncogenesis (Shah et al., "The Hox Genes and Their Roles in Onco-Genesis," *Nat. Rev. Cancer* 10:361-371 (2010), which is incorporated herein by reference in its entirety). Both the ER and TGF-β pathways play a pivotal role in tumor suppression (Bachman et al., "Duel Nature of TGF-β Signaling: Tumor Suppressor vs. Tumor Promoter," *Curr. Opin. Oncol.* 17:49-54 (2005) and Berger et al., "The p53-Estrogen Receptor Loop in Cancer," *Curr. Mol. Med.* 13:1229-1240 (2013), each of which is incorporated herein by reference in its entirety).

TABLE 3

Number of mRNAs Differentially Expressed in Abundance, Polysome Association, or Translational Activity between TamR and TamS Cells with Tamoxifen Treatment

| | | Downregulated | Upregulated |
|---|---|---|---|
| TamR vs. TamS | Abundance | 1864 | 1884 |
| | Polysome association | 2183 | 2187 |
| | Translational activity | 162 | 163 |

P < 0.05, and cut off values of $\log_2$ FC ≥ | 1.0 | for mRNA abundance and $\log_2$ FC ≥ | 0.6 | for polysome association and translational activity.

TABLE 4

Select mRNAs Involved in Developmental Regulation, DNA Recombination/Repair, Cell Cycle Regulation, and Proliferation

| | OMIM number | mRNA Abundance TamR control vs. TamS control | Polysome Association TamR control vs. TamS control |
|---|---|---|---|
| HOX Genes | | | |
| HOXB3 | 142966 | 7.29725045 | 6.70728869 |
| HOXB2 | 142967 | 5.64357484 | 7.270423518 |
| HOXB9 | 142964 | 2.773517243 | 2.922537084 |
| HOXA3 | 142954 | −1.129897644 | Unchanged |
| HOXB7 | 142962 | 1.380021326 | 1.455744033 |
| RUNX Genes | | | |
| RUNX1 | 151385 | Unchanged | Unchanged |
| RUNX2 | 600211 | 3.071215605 | 3.548584092 |
| RUNX3 | 600210 | Unchanged | Unchanged |

TABLE 4-continued

Select mRNAs Involved in Developmental Regulation, DNA Recombination/Repair, Cell Cycle Regulation, and Proliferation

| | OMIM number | mRNA Abundance TamR control vs. TamS control | Polysome Association TamR control vs. TamS control |
|---|---|---|---|
| DNA Repair/Recombination | | | |
| XRCC1 | 194360 | Unchanged | Unchanged |
| XRCC2 | 600375 | Unchanged | Unchanged |
| XRCC3 | 600675 | Unchanged | Unchanged |
| TREX1 | 606609 | −0.910234659 | −1.255442125 |
| RAD51C | 602774 | Unchanged | 0.941923443 |
| NEIL2 | 608933 | 1.698540245 | 1.665681816 |
| BRCA1 | 113705 | Unchanged | 0.62057147 |
| WNT Genes | | | |
| WNT10B | 601906 | 2.075587194 | 1.645830854 |
| CTNND2 | 604275 | −3.661170799 | −3.6088588 |
| FZD7 | 603410 | −1.151071495 | −1.112192957 |
| TGF-β Genes | | | |
| TGFB1 | 190180 | Unchanged | Unchanged |
| TGFB2 | 190220 | −2.974538978 | −2.531500195 |
| TGFB3 | 190230 | Unchanged | Unchanged |
| SMAD3 | 603109 | −1.068350978 | −1.11112183 |
| SMAD2 | 601366 | Unchanged | Unchanged |
| SMAD4 | 600993 | Unchanged | Unchanged |
| Estrogen Receptor Genes | | | |
| ESR1 | 133430 | −2.157502785 | −2.044870266 |
| IGFBP5 | 146734 | −2.161878935 | −2.301950642 |
| TFF1 | 113710 | 1.940260889 | Unchanged |
| FOSB | 164772 | −2.035017448 | −2.215419746 |
| CTGF | 121009 | −2.462035475 | −2.463846673 |
| BMP7 | 112267 | −1.213971924 | −1.36354865 |
| F-box Genes | | | |
| FBXO5 | 606013 | Unchanged | 0.763739364 |
| FBXO48 | N/A | 1.285461978 | 1.106426696 |
| FBXO32 | 606604 | −0.987198635 | −0.955496773 |
| FBXO6 | 605647 | Unchanged | −0.821811601 |
| FBXL12 | 609079 | Unchanged | −0.70180174 | mRNAs differentially expressed in abundance (P ≤ 0.05, $\log_2$ FC ≥ | 1.0 |), or polysomal association (P ≤ 0.05, $\log_2$ FC ≥ | 0.6 |) between resistant and sensitive cells and tamoxifen treatment. Expression values are in $\log_2$ scale.

Figures 9A, 9B, 9C, 9D, 9E, 9F:
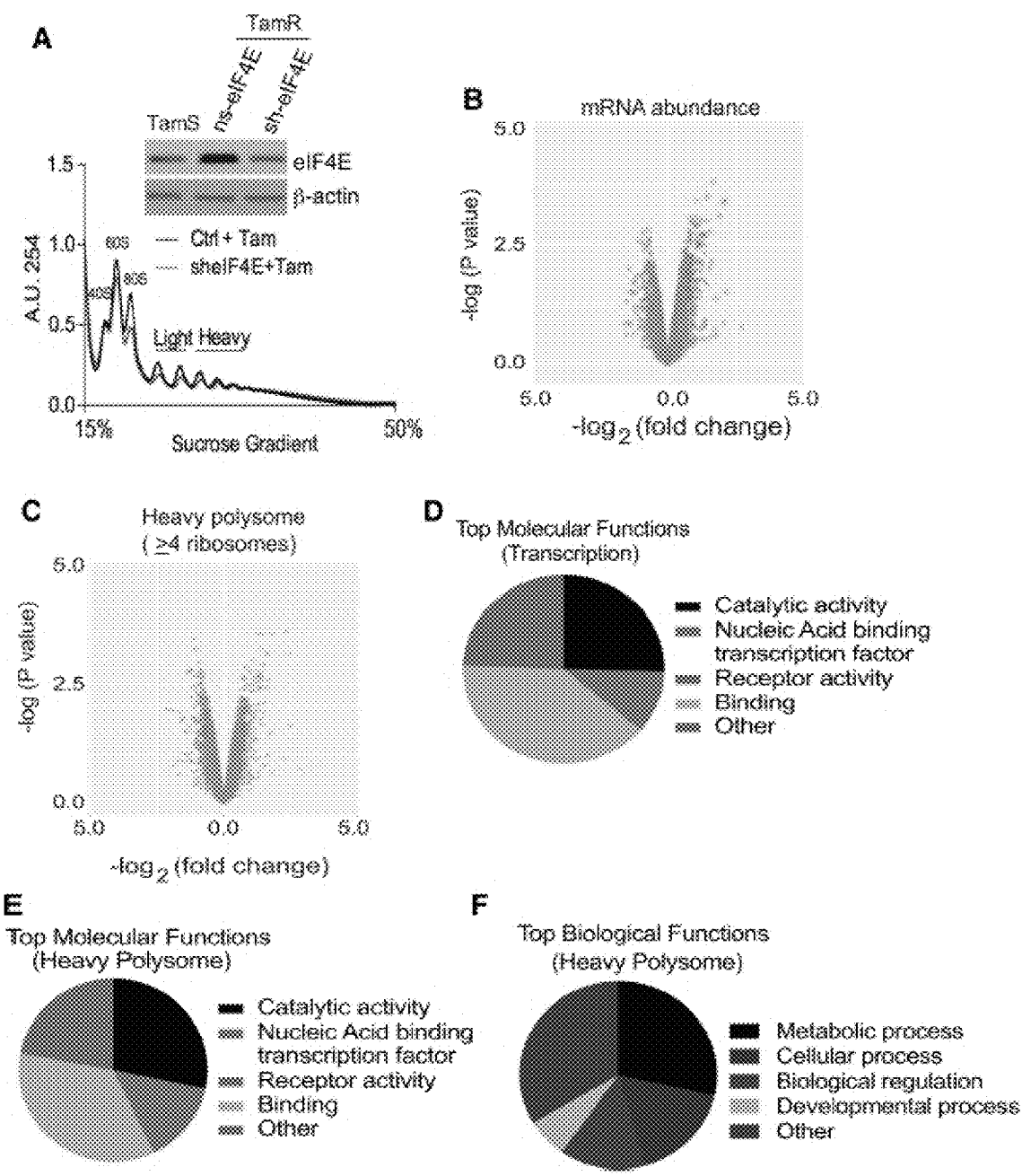
FIGS. 9A-9F show results demonstrating that tamoxifen resistance is associated with eIF4E overexpression and selective mRNA translation.
Figures 10A, 10B, 10C, 10D, 10E, 10F, 10G, 10H:
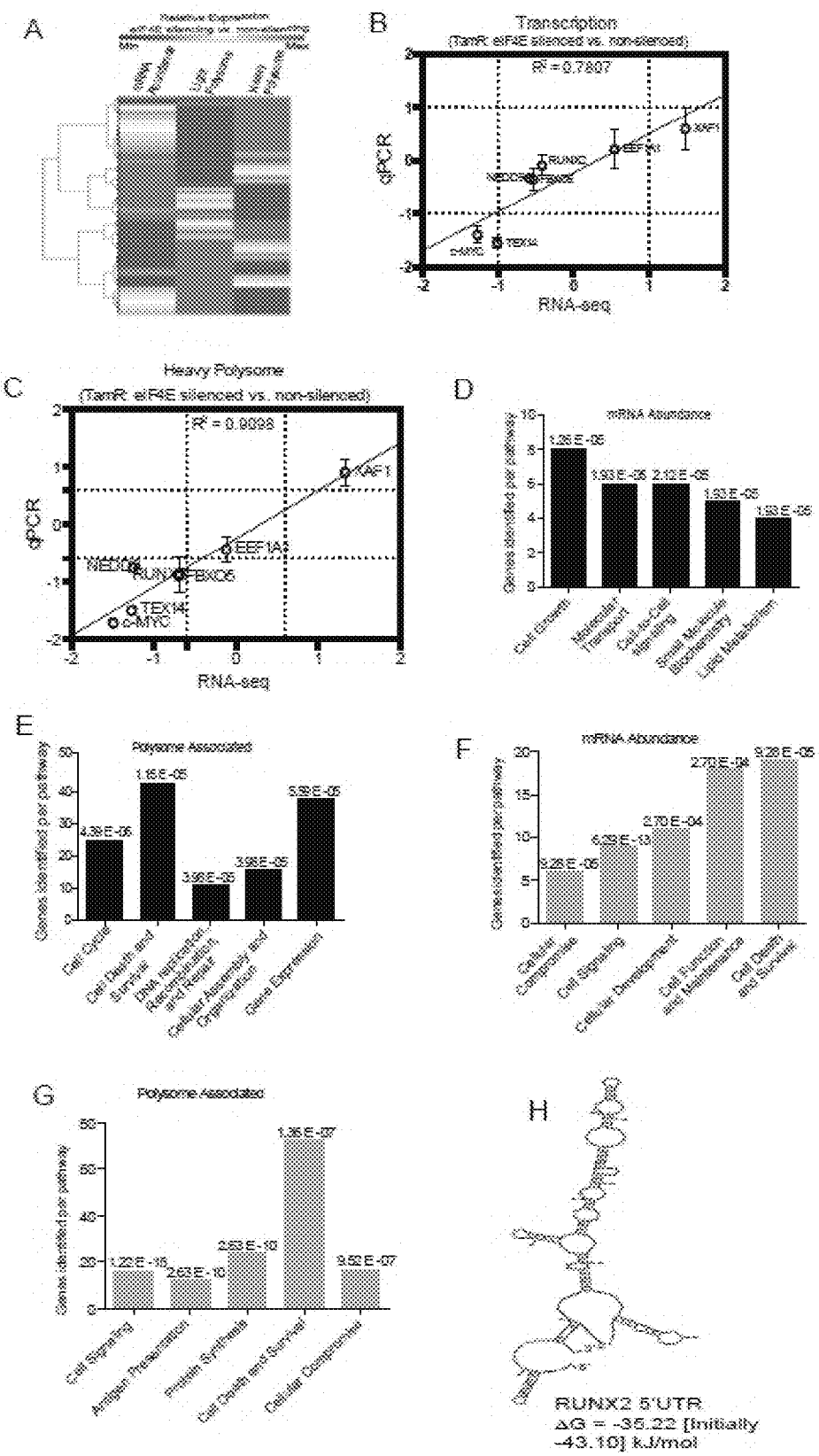
FIGS. 10A-10H show results of genomic and pathway analysis of genes significantly altered in resistant cells with eIF4E silencing.

Example 5—Identification of mRNAs Highly Dependent on Overexpression of P-eIF4E for Translation in Tamoxifen-Resistant Breast Cancer Cells mRNAs associated with tamoxifen resistance that were selectively altered in translation resulting from increased expression, availability, and phosphorylation of eIF4E were next identified. To do so, genome-wide transcriptomic and translatomic analyses were performed in TamR cells with and without modest eIF4E reduction to identify this data set by silencing eIF4E to levels similar to TamS cells (FIG. 9A). Total mRNA and polysomal mRNA profiling showed only a very slight overall reduction in mRNA and polysome content in tamoxifen-resistant cells after eIF4E silencing (FIGS. 9A-9C; FIGS. 10A-10C). Surprisingly, the number of mRNAs that changed significantly only at the translation-specific level was small (with most of them down-regulated) but included a small number that were translationally up-regulated as well (FIG. 9C; FIG. 10A; Table 5). Select genes from RNA-seq analysis were validated by qPCR of total and heavy polysome fractions (FIGS. 10B-10C). GO analyses and Ingenuity Pathway Analyses (IPAs) revealed similar biological and molecular functions for transcriptionally and translationally increased mRNAs associated with tamoxifen resistance (FIGS. 9D-9F; FIGS. 10E-10G).

TABLE 5

Select mRNAs Involved in Genomic Integrity,
Cell Cycle Regulation, and Apoptosis

| Gene ID | OMIM number | mRNA Abundance TamR eIF4E silenced vs. TamR control | Polysome Association TamR eIF4E silenced vs. TamR control |
|---|---|---|---|
| HOXB3 | 142966 | −1.444501351 | −1.660420873 |
| RUNX2 | 600211 | Unchanged | −0.682616001 |
| NEDD9 | 602265 | Unchanged | −1.251773897 |
| FBXO5 | 606013 | Unchanged | −0.69480371 |
| SKP2 | 601436 | Unchanged | Unchanged |
| SERPINE1 | 173360 | −1.081641164 | −0.725553337 |
| TEX14 | 605792 | −1.01105203 | −1.269227578 |
| XAF1 | 606717 | 1.480330624 | 1.328375516 |
| NUPR1 | 614812 | 1.172831121 | 1.112923376 |
| TBX1 | 602054 | 1.143821446 | 1.155209867 |
| AXIN2 | 604025 | Unchanged | −1.433035271 |
| GATA4 | 600576 | Unchanged | Unchanged |
| CHAC1 | 614587 | 1.430900224 | 1.677928504 |
| GREB1 | 611736 | Unchanged | Unchanged |
| EGR3 | 602419 | Unchanged | −0.75822111 |
| CBLC | 608453 | Unchanged | Unchanged |
| DBC1 | 607359 | Unchanged | Unchanged |
| DDIT4 | 607729 | Unchanged | Unchanged |
| OTX1 | 600036 | Unchanged | −0.671383852 |
| ORC1 | 601902 | Unchanged | −0.732645005 |
| MYC | 190080 | −1.272493556 | −1.492840382 |

Differentially expressed mRNAs in abundance ($P \leq 0.05$, $\log_2 FC \geq | 1.0 |$), or polysomal association ($P \leq 0.05$, $\log_2 FC \geq | 0.6 |$) with or without eIF4E silencing and tamoxifen treatment. Expression values are in $\log_2$ scale.

Figures 11A, 11B, 11C, 11D, 11E, 11F, 11G, 11H, 11I, 11J:
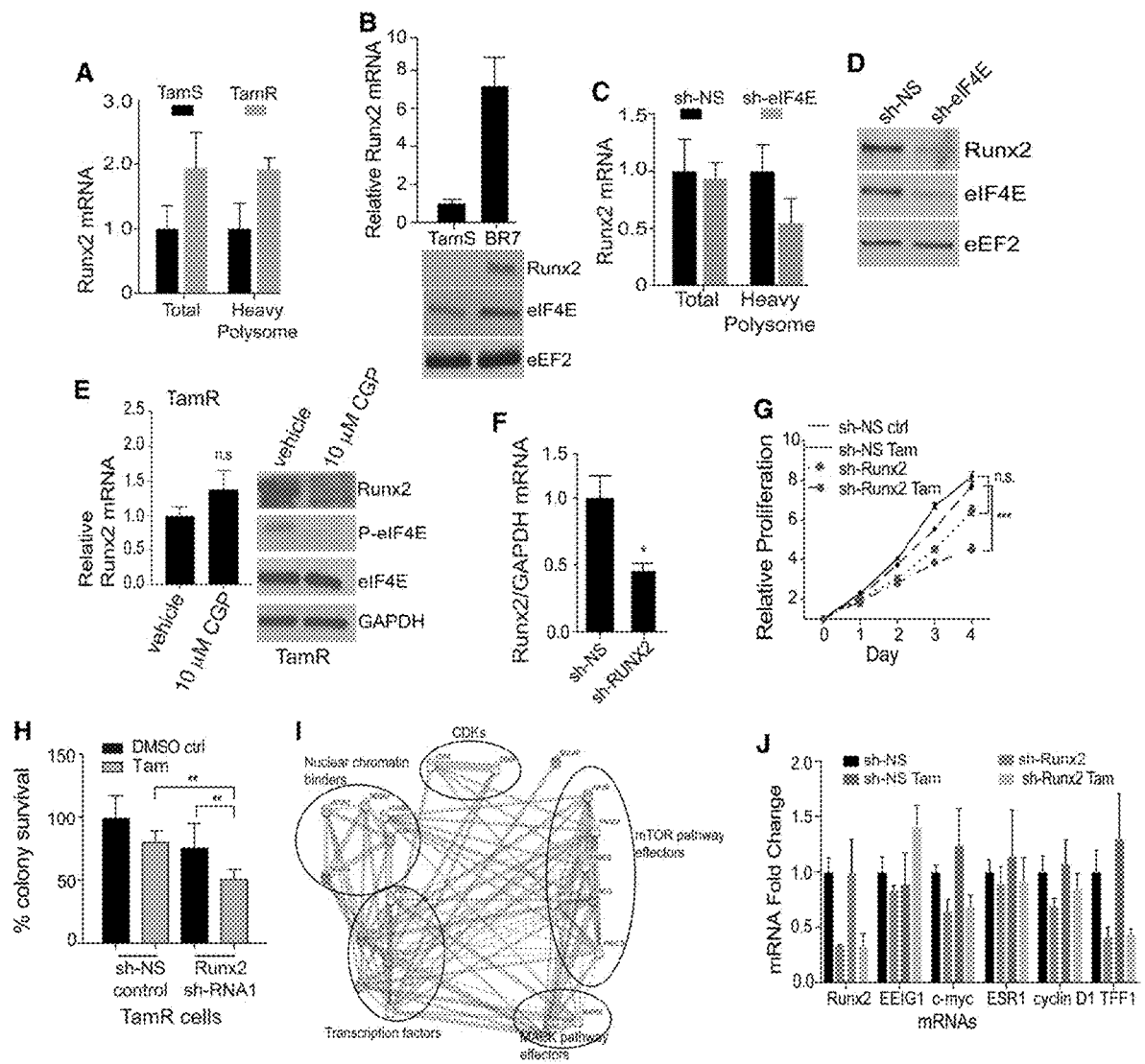
FIGS. 11A-11J shows results demonstrating that silencing Runx2 mRNA partially restores tamoxifen sensitivity to resistant cells.

The biological functions of mRNAs identified as highly eIF4E-dependent in tamoxifen-resistant cells were next assessed. Table 6 lists mRNAs that meet these stringent criteria. Of these, Runx2 was particularly notable because it encodes a protein with a number of activities that could play a role in tamoxifen resistance, as it is an important inhibitor of estrogen signaling and stimulates oncogenic pathways. RUNX2 is a transcription factor involved in regulating cell determination (Young et al., "Mitotic Retention of Gene Expression Patterns by the Cell Fate-Determining Transcription Factor Runx2," *Proc. Natl. Acad. Sci.* 104:3189-3194 (2007) and Blyth et al., "Runx2 in Normal Tissues and Cancer Cells: A Developing Story," *Blood Cells Mol. Dis.* 45:117-123 (2010), each of which is incorporated herein by reference in its entirety) and the TGF-β and Wnt/β-catenin pathways (which are also involved in cancer development, progression, and metastasis) (Young et al., "Mitotic Retention of Gene Expression Patterns by the Cell Fate-Determining Transcription Factor Runx2," *Proc. Natl. Acad. Sci.* 104:3189-3194 (2007) and Yang et al., "Subnuclear Domain Proteins in Cancer Cells Support the Functions of RUNX2 in the DNA Damage Response," *J. Cell Sci.* 128:728 (2015), each of which is incorporated herein by reference in its entirety) and opposes ER signaling, leading to more aggressive ER+ breast cancer (Tandon et al., "Runx2 Activates PI3K/Akt Signaling via mTORC2 Regulation in Invasive Breast Cancer Cells," *Breast Cancer Res.* 16:1-14 (2014), which is incorporated herein by reference in its entirety). Interestingly, recent studies have also shown that RUNX2 plays a crucial role in regulating mammary stem cell regeneration (Ferrari et al., "Runx2 Contributes to the Regenerative Potential of the Mammary Epithelium," *Sci. Rep.* 5:15658 (2015), which is incorporated herein by reference in its entirety). Surprisingly, Runx2 was found to be the only Runx gene within the family to be transcriptionally or translationally up-regulated in both TamR and PDX tamoxifen-resistant cell lines (FIGS. 11A-11B; Table 4). Total Runx2 mRNA levels were unchanged with eIF4E reduction in TamR cells, but heavy polysome association was reduced threefold, which corresponds to a fourfold to fivefold reduction in RUNX2 protein levels (FIGS. 11C-11D). It was also determined whether Runx2 mRNA requires eIF4E S209 phosphorylation by Mnk1. Cells were untreated or treated with CGP57380, and Runx2 mRNA and protein levels were determined. There was no statistically significant difference in Runx2 mRNA levels with drug treatment, whereas RUNX2 protein levels were reduced more than threefold (FIG. 11E). Therefore, increased levels or availability of eIF4E and increased eIF4E S209 phosphorylation by Mnk1 promote selectively increased translation of Runx2 mRNA.

TABLE 6

Number of mRNAs Differentially Expressed in Abundance,
Polysome Association, or Translational Activity
with eIF4E Silencing and Tamoxifen Treatment

| | | Downregulated | Upregulated |
|---|---|---|---|
| TamR eIF4E silenced vs. TamR control | Abundance | 9 | 50 |
| | Polysome association | 168 | 185 |
| | Translational activity | 144 | 21 |

$P < 0.05$, and cut off values of $\log_2 FC \geq | 1.0 |$ for mRNA abundance and $\log_2 FC \geq | 0.6 |$ for polysome association and translational activity.

Figures 12A, 12B, 12C, 12D:
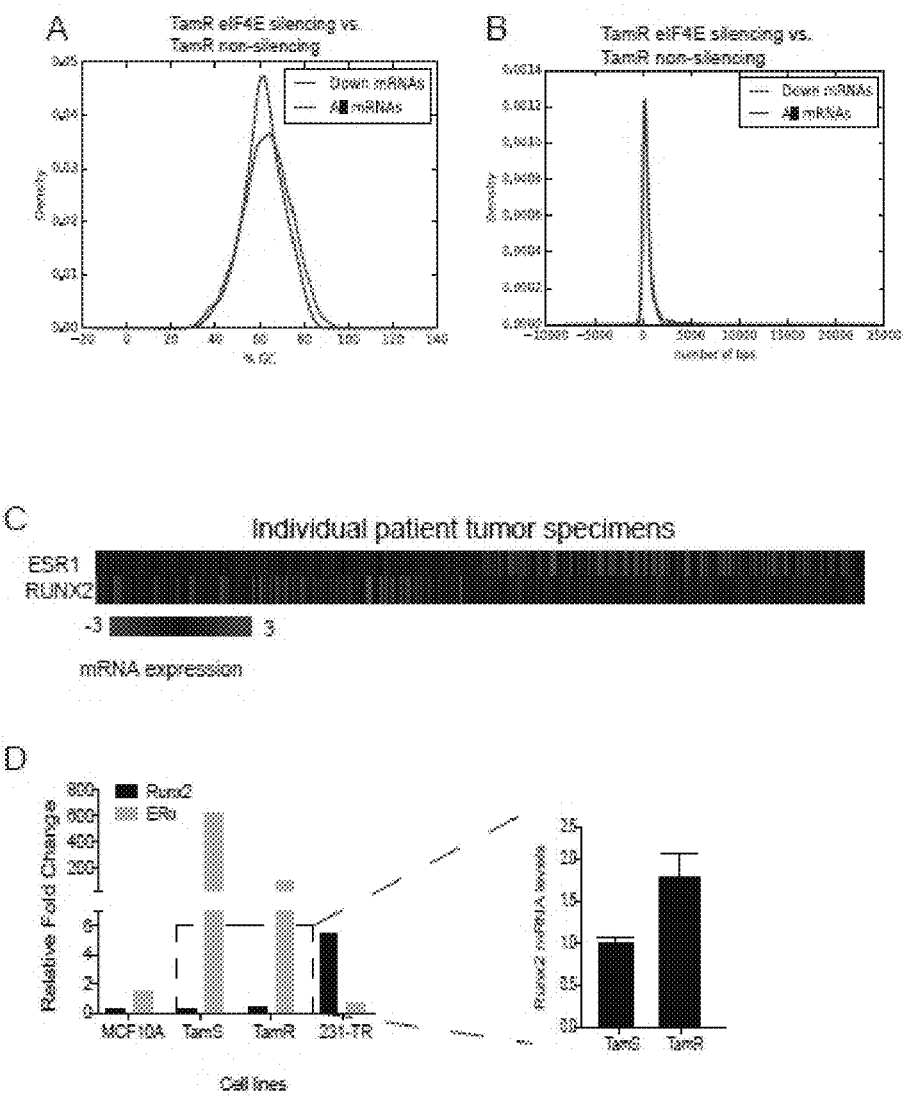
FIGS. 12A-12D show results of genome-wide analysis of 5' UTRs of genes selectively downregulated with eIF4E silencing.

Computational analysis of the Runx2 5' UTR is consistent with a greater eIF4E dependency for translation, showing significant secondary structure and a high GC content within 30 nucleotides of the cap as well as a AG of approximately −40 kcal/mol (FIG. 10H). To this end, whether mRNAs that are translationally down-regulated upon eIF4E reduction have features in their 5' UTRs that dictate a strong dependence on eIF4E levels was investigated. A genome-wide analysis of the 5' UTR of mRNAs translationally down-regulated with eIF4E silencing to the level of tamoxifen-sensitive cells was conducted; however, no statistical differences in GC content or length was observed when compared with all cellular mRNAs (FIGS. 12A-12B). This is consistent with previously published results regarding 5' UTR analysis of translationally altered mRNAs upon eIF4E down-regulation (Truitt et al., "Differential Requirements for eIF4E Dose in Normal Development and Cancer," *Cell* 162:59-71 (2015), which is incorporated herein by reference in its entirety). To investigate the importance of RUNX2 in tamoxifen resistance in ER+ cells, shRNA was used to reduce Runx2 mRNA levels approximately threefold, to levels found in tamoxifen-sensitive TamS cells and TamR cells silenced for eIF4E (FIG. 11F). The threefold reduction in RUNX2 in TamR cells resulted in a strong impairment in proliferation in the presence of tamoxifen (FIG. 11H) as well as a significant reduction in clonogenic cell survival of normally drug-resistant cells (FIG. 11I).

RUNX2 establishes a molecular program that opposes ERα signaling in both the normal and transformed settings (Chimge et al., "The RUNX Family in Breast Cancer: Relationships with Estrogen Signaling," *Oncogene* 32:2121-2130 (2013) and McDonald et al., "RUNX2 Correlates with Subtype-Specific Breast Cancer in a Human Tissue Microarray, and Ectopic Expression of Runx2 Perturbs Differentiation in the Mouse Mammary Gland," *Dis. Model Mech.* 7:525 (2014), each of which is incorporated herein by reference in its entirety). In support of these studies, using computational STRING analysis, interactions between RUNX2 and ERα, including established tamoxifen resistance genes, were identified (FIG. 11I). Furthermore, ERα-RUNX2 interaction analysis is consistent with RUNX2 stimulation of both the mTORC1 and MAPK translational control pathways (FIG. 11I) to promote drug resistance. In fact, it has been reported that breast tumors expressing high levels of RUNX2 generally express low levels of ERα and vice versa. To this end, an extensive bioinformatics search of the TCGA (The Cancer Genome Atlas) breast cancer database as well as analysis of breast cancer cell lines was performed. An almost perfect inverse correlation between ERα (ESR1) and Runx2 mRNA expression was found in 594 patients diagnosed with ER$^+$ breast cancer (FIGS. 12C-12D). To understand the significance of the RUNX2-ERα axis in relation to tamoxifen responsiveness, whether silencing Runx2 in TamR cells reverses the RUNX2 blockade of canonical ERα signaling as a mechanism to reestablish drug sensitivity was investigated. qRT-PCR analysis of ER target genes indicated that re-duction of RUNX2 did not restore ERα signaling in resistant cells (FIG. 11J), indicating that RUNX2 expression may permanently overwrite classical ERα signaling, leading to genomic changes that establish permanent anti-estrogen resistance.

Discussion of Examples 1-5

The majority of ER$^+$ breast cancer patients treated with tamoxifen will relapse with resistant disease even decades after curative care (Ali et al., "Endocrine-Responsive Breast Cancer and Strategies for Combating Resistance," *Nat. Rev. Cancer* 2:101-112 (2002), which is incorporated herein by reference in its entirety). Evidence has shown that a cross-talk exists between the ER and the PI3K/Akt/mTOR and MAPK signaling pathways in promoting tamoxifen resistance (Sommer et al., "Estrogen Receptor and Breast Cancer," *Semin. Cancer Biol.* 11:339-352 (2001) and Fan et al., "A Molecular Model for the Mechanism of Acquired Tamoxifen Resistance in Breast Cancer," *Eur. J. Cancer* 50:2866-2876 (2014), each of which is incorporated herein by reference in its entirety). The results of Examples 1-5 described herein indicate that tamoxifen resistance also involves the mRNA translational regulation of these pathways and is manifested by increased eIF4E levels, availability, and phosphorylation, resulting in selective mRNA translational reprogramming that establishes an anti-ER and anti-estrogen signaling state. Furthermore, these results have broader implications in understanding resistance to other endocrine therapies; notably, resistance to aromatase inhibitors. While aromatase inhibitors are also clinically used for the treatment of metastatic ER$^+$ breast cancers, resistance occurs and is thought to arise through mechanisms similar to tamoxifen; namely, mTORC1 inhibition in combination with aromatase inhibitors leads to an overall increase in patient survival similar to results obtained in this and other studies regarding anti-estrogen resistance.

Alterations in eIF4E-dependent translation can promote selective translation of mRNAs that reprogram cancer cells for survival, invasion, metastasis, and possibly drug resistance (Silvera et al., "Essential Role for eIF4GI Overexpression in the Pathogenesis of Inflammatory Breast Cancer," *Nat. Cell Biol.* 11:903-908 (2009); Hsieh et al., "The Translational Landscape of mTOR Signalling Steers Cancer Initiation and Metastasis," *Nature* 485:55-61 (2012); and Boussemart et al., "eIF4F is a Nexus of Resistance to Anti-BRAF and Anti-MEK Cancer Therapies," *Nature* 513:105-109 (2014), each of which is incorporated herein by reference in its entirety). A causal role for selective mRNA translation in therapy resistance in breast and other cancers was previously demonstrated (Braunstein et al., "Regulation of Protein Synthesis by Ionizing Radiation," *Mol. Cell. Biol.* 29:5645-5656 (2009); Ramirez-Valle et al., "Mitotic Raptor Promotes mTORC1 Activity, G(2)/M Cell Cycle Progression, and Internal Ribosome Entry Site-Mediated mRNA Translation," *Mol. Cell. Biol.* 30:3151-3164 (2010); Badura et al., "DNA Damage and eIF4G1 in Breast Cancer Cells Reprogram Translation for Survival and DNA Repair mRNAs," *Proc. Natl. Acad. Sci.* 109:18767-18772 (2012); and Korets et al., "Dual mTORC1/2 Inhibition in a Preclinical Xenograft Tumor Model of Endometrial Cancer," *Gynecol. Oncol.* 132:468-473 (2014), each of which is incorporated herein by reference in its entirety). The present application discloses a mechanism by which increased expression, availability, and phosphorylation of eIF4E form a regulatory nexus important in anti-estrogen resistance in ER$^+$ breast cancer. During therapeutic treatment, when cell surface EGF and IGF receptors are activated, they transactivate downstream MAPK/ERK/MNK and PI3K/Akt/mTOR pathways and ultimately converge on eIF4E, increasing its activity, phosphorylation, and availability. This leads to eIF4E-mediated selective translation of key mRNAs, such as Runx2. Genome-wide transcription/translation analysis of tamoxifen-resistant cells revealed that several key pathways are down-regulated upon eIF4E silencing, with a majority of the down-regulated pathways with eIF4E silencing involved in cellular organization and motility, genetic recombination, and developmental processes (Ramirez-Valle et al., "eIF4GI Links Nutrient Sensing by mTOR to Cell Proliferation and Inhibition of Autophagy," *J. Cell Biol.* 181:293-307 (2008) and Cao et al., "Functional Role of Eukaryotic Translation Initiation Factor 4γ1 (EIF4G1) in NSCLC," *Oncotarget* 7:24242-24251 (2016), each of which is incorporated herein by reference in its entirety). Most of these mRNAs are involved in DNA-protein interactions and the regulation of transcription factor binding. From these findings, RUNX2 was identified at the intersection of these molecular functions and a strong translational down-regulation with eIF4E silencing was demonstrated in tamoxifen-resistant cells.

RUNX2 belongs to the family of RUNX transcription factors (RUNX1, 2, 3), which are involved in lineage-specific cell fate determination that is recapitulated in cellular transformation and tumorigenesis. RUNX proteins regulate gene expression by functioning as molecular scaffolds to recruit chromatin remodeling enzymes (e.g., SWI/SNF and CTCF) and modulate promoter accessibility (Young et al., "Mitotic Retention of Gene Expression Patterns by the Cell Fate-Determining Transcription Factor Runx2," *Proc. Natl. Acad. Sci.* 104:3189-3194 (2007) and Wu et al., "Genomic Occupancy of Runx2 with Global Expression Profiling Identifies a Novel Dimension to Control of Osteoblastogenesis," *Genome Biol.* 15:R52 (2014), each of which is incorporated herein by reference in its entirety). Studies involving the role of RUNX2 in breast cancer have demonstrated the importance of overexpression of RUNX2 in regulating tumor growth, epithelial-mesenchymal transition, and metastasis (Pratap et al., "Ectopic Runx2 Expression in Mammary Epithelial Cells Disrupts Formation of Normal Acini Structure: Implications for Breast Cancer Progression," *Cancer Res.* 69:6807-6814 (2009); Chimge et al., "Regulation of Breast Cancer Metastasis by Runx2 and Estrogen Signaling: The Role of SNAI2," *Breast Cancer Res.* 13:R127 (2011); Karlin et al., "The Oncogenic STP Axis Promotes Triple-Negative Breast Cancer via Degradation of the REST Tumor Suppressor," *Cell Rep.* 9:1318-1332 (2014), each of which is incorporated herein by reference in its entirety). Furthermore, RUNX2 has been shown to regulate the expression of genes involved in WNT/β-catenin and TGF-βsignaling—two key pathways known to be dysregulated in many cancers, particularly breast cancer (Chimge et al., "The RUNX Family in Breast Cancer: Relationships with Estrogen Signaling," *Oncogene* 32:2121-2130 (2013) and Ferrari et al., "Runx2 Contributes to the Regenerative Potential of the Mammary Epithelium," *Sci. Rep.* 5:15658 (2015), each of which is incorporated herein by reference in its entirety). Importantly, WNT and TGF-β signaling has been shown to promote cancer progression to a more poorly differentiated state (Barcellos-Hoff et al., "Transforming Growth Factor-0 in Breast Cancer: Too Much, Too Late," *Breast Cancer Res.* 11:202 (2009) and Ferrari et al., "Runx2 Contributes to the Regenerative Potential of the Mammary Epithelium," *Sci. Rep.* 5:15658 (2015), each of which is incorporated herein by reference in its entirety). Notably, other studies describing RUNX2 transcriptional activity have shown that it regulates ER signaling by direct and indirect interactions (McDonald et al., "RUNX2 Correlates with Subtype-Specific Breast Cancer in a Human Tissue Microarray, and Ectopic Expression of Runx2 Perturbs Differentiation in the Mouse Mammary Gland," *Dis. Model Mech.* 7:525 (2014) and Jeselsohn et al., "Embryonic Transcription Factor SOX9 Drives Breast Cancer Endocrine Resistance," *Proc. Natl. Acad. Sci.* 114: E4482-E4491 (2017), each of which is incorporated herein by reference in its entirety). Thus, the Examples of the present application demonstrate that established genes and signaling pathways that confer tamoxifen resistance (and possibly other forms of endocrine therapy resistance) do so by acting on eIF4E abundance and phosphorylation to selectively translationally reprogram the breast cancer cell for estrogen- and ER-opposing activities.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of increasing sensitivity of estrogen receptor positive (ER$^+$) breast cancer cells to treatment with an endocrine therapy, the method comprising:
   selecting ER$^+$breast cancer cells, and
   administering to the selected cells (i) one or more mammalian target of rapamycin (mTOR) inhibitors and (ii) one or more MAP kinase-interacting serine/threonine-protein kinase 1(MNK1) inhibitors in an effective amount to increase the sensitivity of the ER$^+$breast cancer cells to treatment with the endocrine therapy.

2. The method according to claim 1, wherein the one or more mTOR inhibitors comprises rapamycin (sirolimus, Rapamune®), everolimus (Affinitor® or RAD001), temsirolimus (Torisel®, CCI-779, NSC 683864), tacrolimus (FK506), ridaforolimus (AP23573, MK-8669, deforolimus), dactolisib (BEZ235, NVP-BEZ235), AZD8055, KU-0063794, sapanisertib (INK 128, MLN0128), voxtalisib (XL765, SAR245409), Torin 1, OSI-027, PF-04691502, apitolisib (GDC-0980, RG7422), GSK1059615, gedatolisib (PF-05212384, PKI-587), WYE-354, vistusertib (AZD2014), Torin 2, WYE-125132 (WYE-132), BGT226 (NVP-BGT226), WYE-687, WAY-600, Palomid 529 (P529), ETP-46464, GDC-0349, XL388, CC-115, CC-223, zotarolimus (ABT-578), GDC-0084, CZ415, SF1126, SF2523, LY3023414, MHY1485, PI-103, Torkinib (PP242), chrysophanic acid, or a combination thereof.

3. The method according to claim 1, wherein the one or more MNK1 inhibitors comprises BAY 1143269, CGP57380, CGP052088, ETP 45835 dihydrochloride, eFT-508, or a combination thereof.

4. The method according to claim 1, wherein said method increases the sensitivity of the ER$^+$breast cancer cells to treatment with a selective estrogen receptor modulator (SERM), an aromatase inhibitor, and/or a selective estrogen receptor degrader (SERD).

5. The method according to claim 1, wherein the selected cells exhibit resistance to treatment with the endocrine therapy prior to said administering.

6. The method according to claim 1 further comprising:
   administering one or more endocrine therapies to the selected cells.

7. The method according to claim 6, wherein said administering the one or more endocrine therapies to the selected cells reduces growth, an invasive property, or a metastatic property of the selected cells.

8. The method according to claim 1, wherein the method is carried out in vitro.

9. The method according to claim 1, wherein the method is carried out in vivo.

10. The method according to claim 9, wherein said selecting comprises selecting a subject having ER$^+$breast cancer and said administering is to the selected subject.

11. The method according to claim 10, wherein the selected subject exhibits resistance to treatment with the endocrine therapy prior to said administering.

12. The method according to claim 10 further comprising:
    administering one or more endocrine therapies to the selected subject.

13. The method according to claim 12, wherein said administering of (i) the one or more mTOR inhibitors and (ii) the one or more MNK1 inhibitors is carried out prior to said administering of the one or more endocrine therapies to the selected subject.

14. A method of treating a subject having ER$^+$breast cancer, the method comprising:
    selecting a subject having ER$^+$breast cancer, wherein the ER$^+$breast cancer exhibits resistance to treatment with an endocrine therapy, and
    administering to the selected subject (i) one or more mTOR inhibitors, (ii) one or more MNK1 inhibitors, and (iii) one or more endocrine therapies.

15. The method according to claim 14, wherein the one or more mTOR inhibitors comprises rapamycin (sirolimus, Rapamune®), everolimus (Affinitor® or RAD001), temsirolimus (Torisel®, CCI-779, NSC 683864), tacrolimus (FK506), ridaforolimus (AP23573, MK-8669, deforolimus), dactolisib (BEZ235, NVP-BEZ235), AZD8055, KU-0063794, sapanisertib (INK 128, MLN0128), voxtalisib (XL765, SAR245409), Torin 1, OSI-027, PF-04691502, apitolisib (GDC-0980, RG7422), GSK1059615, gedatolisib (PF-05212384, PKI-587), WYE-354, vistusertib (AZD2014), Torin 2, WYE-125132 (WYE-132), BGT226 (NVP-BGT226), WYE-687, WAY-600, Palomid 529 (P529), ETP-46464, GDC-0349, XL388, CC-115, CC-223, zotarolimus (ABT-578), GDC-0084, CZ415, SF1126, SF2523, LY3023414, MHY1485, PI-103, Torkinib (PP242), chrysophanic acid, or a combination thereof.

16. The method according to claim 14, wherein the one or more MNK1 inhibitors comprises BAY 1143269, CGP 57380, CGP 052088, ETP 45835 dihydrochloride, eFT-508, or a combination thereof.

17. The method according to claim 14, wherein said resistance is to treatment with a SERM, an aromatase inhibitor, and/or a SERD.

18. The method according to claim 14, wherein said administering reduces tumor growth, invasiveness, progression, recurrence, and/or metastasis of the ER$^+$breast cancer in the selected subject.

19. The method according to claim 14, wherein said administering of (i) and (ii) is carried out prior to said administering of (iii).

20. The method according to claim 14, wherein the selected subject is a mammal.

\* \* \* \* \*